United States Patent [19]
Arrhenius et al.

[11] Patent Number: 6,103,870
[45] Date of Patent: *Aug. 15, 2000

[54] CS-1 PEPTIDOMIMETIC, COMPOSITIONS AND METHODS OF USING THE SAME

[75] Inventors: Thomas S. Arrhenius; Mariano J. Elices, both of San Diego; Federico C. A. Gaeta, Olivenhain, all of Calif.

[73] Assignee: Cytel Corporation, San Diego, Calif.

[*] Notice: This patent is subject to a terminal disclaimer.

[21] Appl. No.: 08/923,026

[22] Filed: Sep. 3, 1997

Related U.S. Application Data

[63] Continuation of application No. 08/435,286, May 5, 1995, Pat. No. 5,688,913, which is a continuation of application No. 08/164,101, Dec. 6, 1993, abandoned.

[51] Int. Cl.$^7$ .................................................. A61K 38/06
[52] U.S. Cl. ........................... 530/331; 530/330; 514/18; 514/19
[58] Field of Search ....................... 514/18, 19; 530/331, 530/330

[56] References Cited

U.S. PATENT DOCUMENTS

| | | | |
|---|---|---|---|
| 4,564,616 | 1/1986 | Jones et al. | 514/260 |
| 4,822,606 | 4/1989 | Snyderman et al. | 424/88 |
| 5,294,511 | 3/1994 | Furcht et al. | 435/240.242 |
| 5,294,551 | 3/1994 | Furcht et al. | 435/240.242 |
| 5,340,802 | 8/1994 | Shiosaki et al. | 514/18 |
| 5,387,504 | 2/1995 | Mumford | 435/7.1 |

FOREIGN PATENT DOCUMENTS

| | | |
|---|---|---|
| 0188947 | 7/1986 | European Pat. Off. . |
| 0405506 | 1/1991 | European Pat. Off. . |
| WO 91/03252 | 3/1991 | European Pat. Off. ....... A61K 37/10 |
| WO 93/12809 | 7/1993 | European Pat. Off. ....... A61K 37/02 |
| WO92/13887 | 8/1992 | WIPO . |
| WO93/12809 | 7/1993 | WIPO . |

OTHER PUBLICATIONS

Galleyrand, Peptides 519, 1992.

Komoriya, Akira et al., "The Minimal Essential Sequence for a Major Cell Type–specific Adhesion Site (CS1) within the Alternatively Splice Type III Connecting Segment Domain of Fibronectin is Leucine–Aspartic Acid–Valine." *J. Biol. Chem.* 266:15075–15079 (1991).

Elices, Mariano "The Integrin $\alpha_4\beta_1$ (VLA–4) as a Therapeutic Target." *Cell Adhesion and Human Disease.* Wiley, Chichester (Ciba Foundation Symposium 189) pp. 79–90 (1995).

Nowlin, Dawn M., "A Novel Cyclic Pentapeptide Inhibits $\alpha 4\beta 1$ and $\alpha 5\beta 1$ Integrin–mediated Cell Adhesion." *J. Biol. Chem.* 268:20352–20359 (1993).

Mousa, Shaker A. et al., "Antiplatelet Efficacy and Specificity of DMP728, a Novel Platelet GP11b/IIIa Receptor Antagonist." *Clin. Pharm.* 83:374–382 (1993).

Pfaff, Martin et al., "Selective Recognition of Cyclic RGD Peptides of NMR Defined Conformation by $\alpha V\beta 3$, $\alpha 5\beta 1$ Integrins." *J. Biol. Chem.* 269:20233–20238 (1994).

Iorio et al., "Synthesis, Stereo chemistry, and Biological Activity of the 1–(1–Phenyl–2–methyl-cyclohexyl)piperidines and the 1–(1–Phenyl–4–methylcyclohexyl) piperidines. Absolute Configuration of the Potent trans–(—)–1–(1–Phenyl–2–methylcyclohexyl)piperidine," *J.Med. Chem.*, 34:2615–2623 (1991).

Esser, F. and Roos, O. "N–terminal Cyclization of Peptides with N,N'–Carbonyldiimidazole or N,N'–Thiocarbonyldiimidaxole"*Angew. Chem. Int. Ed. Engl.* 17(6):467–468 (1978).

Komoriya et al., "minimal essential sequence for a Major cell Type specific adhesion site (CS1) within the alternatively sliced type III connecting segment domain of fibronectin is leucine–aspartic acid Valine, " *J. Biol. Chem.* 266:15075–15079 (1991).

*Primary Examiner*—Cecilia J. Tsang
*Assistant Examiner*—David Lukton
*Attorney, Agent, or Firm*—Campbell & Flores LLP

[57] ABSTRACT

The present invention contemplates a peptide that inhibits the binding between the VLA-4 receptor expressed on inflammatory leukocytes and the fibronectin CS-1 peptide expressed on endothelial cells that are involved in immunoinflammatory disease states. Pharmaceutical compositions containing a contemplated peptide and processes for treating immunoinflammatory conditions using a binding-inhibitory peptide are also disclosed.

28 Claims, 6 Drawing Sheets

CS-1 PEPTIDOMIMETIC, COMPOSITIONS AND METHODS OF USING THE SAME

This application is a continuation of application Ser. No. 08/435,286, filed May 5, 1995, now U.S. Pat. No. 5,688,913 which is a continuation of application Ser. No. 08/164,101, filed Dec. 6, 1993, now abandoned.

TECHNICAL FIELD

The present invention relates to binding of inflammatory cells to endothelial cells that express the CS-1 portion of fibronectin on their surfaces, and more particularly to the inhibition of that binding by peptidomimetic compounds of minimal length.

BACKGROUND ART

The immune response relies on leukocyte trafficking and immune surveillance as one of the underpinnings of host defense. Not only does this immune surveillance allow leukocytes to recirculate through lymphoid tissues normally, but also permits rapid leukocyte recruitment and extravasation to adjacent tissues at sites of inflammation. The $\alpha 4\beta 1$ (CD49d/CD29, VLA-4) cell adhesion receptor is an active participant in these leukocyte trafficking functions [Hemler, *Ann. Rev. Immunol.*, 8:365–400 (1990); Hemler et al., *Immunol. Rev.*, 114:45–65 (1990)].

The VLA-4 integrin heterodimer was discovered independently by three research groups and identified as a surface antigen on lymphocytes [Sanchez-Madrid et al., *Eur. J. Immunol.*, 16:1343–1349 (1986); Clayberger et al., *J. Immunol.*, 138:1510–1514 (1987); Hemler et al., *J. Biol. Chem.*, 262:11478–11485 (1987)]. Within the integrin family, VLA-4 is unique on several counts: (i) in contrast to related members of the β1 subfamily, VLA-4 is predominantly expressed on cells of the hematopoietic lineage [Hemler, *Ann. Rev. Immunol.*, 8:365–400 (1990)], and is functionally involved in cell-cell, as well as cell-extracellular matrix (ECM) adhesive interactions [Hemler, *Ann. Rev. Immunol.*, 8:365–400 (1990)]; (ii) despite sequence homology with other integrin α subunits, the α4 subunit stands apart from the two major structural clusters of α subunits because α4 lacks an inserted I-domain, and does not undergo post-translational cleavage near the transmembrane region [Hemler, *Ann. Rev. Immunol.*, 8:365–400 (1990); Hynes, *Cell*, 69:11–25 (1992)]; and (iii) α4 contains a trypsin-like cleavage site that results in cell type-specific surface expression of at least two different structural variants termed α4-150 and α4-80/70 [Pulido et al., *FEBS Lett.*, 294:121–124 (1991); Teixido et al., *J. Biol. Chem.*, 267:1786–1791 (1992); Rubio et al., *Eur. J. Immunol.*, 22:1099–1102 (1992)].

The VLA-4 integrin appears to be one of the earliest adhesion receptors found on CD34-expressing hematopoietic stem cells [Teixido et al., *J. Clin. Invest.*, 90:358–367 (1992)]. However, VLA-4 is expressed only on mature T and B lymphocytes, natural killer (NK) cells, monocytes, basophils and eosinophils, but not on erythrocytes, platelets and neutrophils [Hemler, *Ann. Rev. Immunol.*, 8:365–400 (1990); Gismondi et al., *J. Immunol.*, 146:384–392 (1991); Walsh et al., *J. Immunol.*, 146:3419–3423 (1991); Bochner et al., *J. Exp. Med.*, 173:1553–1556 (1992); Dobrina et al., *J. Clin. Invest.*, 88:20–26 (1991); Weller et al., *Proc. Natl. Acad. Sci. USA*, 88:7430–7433 (1991)].

To date, most adhesion functions mediated by VLA-4 can be explained by a direct molecular interaction between the VLA-4 integrin and either of two separate counterreceptor structures, namely, the cytokine-inducible vascular cell adhesion molecule-1 (VCAM-1) [Elices et al., *Cell*, 60:577–584 (1990); Rice et al., *J. Exp. Med.*, 171:1369–1374 (1990); Schwartz et al., *J. Clin. Invest.*, 85:2019–2022 (1990); Carlos et al., *Blood*, 76:965–970 (1990)], and a subset of the ubiquitous ECM protein fibronectin [Wayner et al., *J. Cell Biol.*, 109:1321–1330 (1989); Guan et al., *Cell*, 60:53–61 (1990); Ferreira et al., *J. Exp. Med.*, 171:351–356 (1990); Elices et al., *Cell*, 60:577–584 (1990)].

VCAM-1 is a member of the immunoglobulin (Ig) gene superfamily [Osborn et al., *Cell*, 59:1203–1211 (1989); Rice et al., *Science*, 246:1303–1306 (1989)] that is expressed predominantly in vascular endothelium in response to pro-inflammatory cytokines such as IL-1, TNFα, and IL-4 [Osborn et al., *Cell*, 59:1203–1211 (1989); Rice et al., *Science*, 246:1303–1306 (1989); Thornhill et al., *J. Immunol.*, 145:865–872 (1990); Masinovsky et al., *J. Immunol.*, 145:2886–2895 (1990); Thornhill et al., *J. Immunol.*, 146:592–598 (1991); Schleimer et al., *J. Immunol.*, 148:1086–1092 (1992); Birdsall et al., *J. Immunol.*, 148:2717–2723 (1992); Swerlick et al., *J. Immunol.*, 149:798–705 (1992); Briscoe et al., *J. Immunol.*, 149:2954–2960 (1992)]. The VLA-4 binding sites on VCAM-1 have been mapped to the outermost N-terminal (first) Ig-like region of the 6-Ig-like domain VCAM-1 isoform [Taichman et al., *Cell Regul.*, 2:347–355 (1991); Vonderheide et al., *J. Exp. Med.*, 175:1433–1442 (1992); Osborn et al., *J. Exp. Med.*, 176:99–107 (1992)], and the first and fourth N-terminal Ig-like regions of the 7-Ig-like domain VCAM-1 isoform [Vonderheide et al., *J. Exp. Med.*, 175:1433–1442 (1992); Osborn et al., *J. Exp. Med.*, 176:99–107 (1992)]. Discrete amino acid sequences within the two separate Ig-like domains in VCAM-1 recognized by the VLA-4 integrin remain to be defined.

In contrast, a high affinity peptide recognition sequence for VLA-4 within fibronectin (FN) has been identified [Wayner et al., *J. Cell. Biol.*, 109:1321–1330 (1989); Ferreira et al., *J. Exp. Med.*, 171:351–356 (1990); Guan et al., *Cell*, 60:53–61 (1990); Mould et al., *J. Biol. Chem.*, 265:4020–4024 (1990); Garcia-Pardo et al., *J. Immunol.*, 144:3361–3366 (1990); Komoriya et al., *J. Biol. Chem.*, 266:15075–15079 (1991)]. That sequence comprises a 25-amino acid residue stretch, termed CS-1 [Humphries et al., *J. Cell Biol.*, 103:2637–2647 (1986); Humphries et al., *J. Biol. Chem.*, 262:6886–6892 (1987)].

The FN gene contains three separate exons termed EIIIA, EIIIB and V or IIICS, which are subject to alternative splicing [Hynes, "Fibronectin", Springer-Verlag, New York (1990)]. The presence of additional acceptor and donor splice signals within the IIICS region permits generation of increased diversity in FN by virtue of multiple IIICS polypeptide variants, for instance, five in human FN [Vibe-Pedersen et al., *FEBS Lett.*, 207:287–291 (1987); Hershberger et al., *Mol. Cell. Biol.*, 10:662–671 (1990)]. Consequently, only a subset of these molecular variants expresses the 25-amino acid CS-1 sequence recognized by VLA-4 [Wayner et al., *J. Cell. Biol.*, 109:1321–1330 (1989); Guan et al., *Cell*, 60:53–61 (1990)].

A minimal essential sequence for specific VLA-4 recognition of CS-1 has been identified as the tripeptide Leu-Asp-Val (LDV) [Komoriya et al., *J. Biol. Chem.*, 266:15075–15079 (1991); Wayner et al., *J. Cell. Biol.*, 116:489–497 (1992); Wayner WO 91/03252 published Mar. 21, 1991; Wayner WO 93/12809 published Jul. 8, 1993; and Humphries WO 92/13887, published Aug. 20, 1992] albeit VLA-4 binds to LDV with at least two orders of magnitude lower affinity than to the native CS-1 25-mer. Nowlin et al., *J. Biol. Chem.*, 268(1):20352–20359 (1993) recently described a cystine-linked cyclic pentapeptide said to inhibit binding by both the Arg-Gly-Asp and CS-1 regions of fibronectin.

VLA-4 shares with other members of the β1 integrin subfamily the ability to promote binding and penetration of microbial pathogens into mammalian cells. Thus, specific interactions of β1 integrins with the bacterial protein invasin [Isberg et al., *Cell*, 60:861–871 (1990); Ennis et al., *J. Exp. Med.*, 177:207–212 (1993)], as well as the protozoan *Trypanosoma cruzi* [Fernandez et al., *Eur. J. Immunol.*, 23:552–557 (1993)] have been described.

A multitude of in vitro studies suggest interactions of VLA-4 with its two known ligands, VCAM-1 and CS-1 FN, have profound biological significance. For instance, VLA-4 binding to VCAM-1 has been demonstrated in adhesion to cytokine-stimulated vascular endothelium by lymphocytes [Elices et al., *Cell*, 60:577–584 (1990); Rice et al., *J. Exp. Med.*, 171:1369–1374 (1990); Schwartz et al., *J. Clin. Invest.*, 85:2019–2022 (1990); Carlos et al., *Blood*, 76:965–970 (1990); Shimizu et al., *J. Cell Biol.*, 113:1203–1212 (1991)], monocytes [Carlos et al., *Blood*, 77:2266–2271 (1991); Jonjic et al., *J. Immunol.*, 148:2080–2083 (1992)], natural killer (NK) cells [Allavena et al., *J. Exp. Med.*, 173:439–448 (1991)], and eosinophils [Walsh et al., *J. Immunol.*, 146:3419–3423 (1991); Bochner et al., *J. Exp. Med.*, 173:1553–1556 (1992); Dobrina et al., *J. Clin. Invest.*, 88:20–26 (1991); Weller et al., *Proc. Natl. Acad. Sci. USA*, 88:7430–7433 (1991)]. Because of its involvement in mediating leukocyte-endothelial attachment, VLA-4/VCAM-1 interactions are considered key in inflammation.

The VLA-4/CS-1 interaction, in turn, has been widely documented in hematopoiesis where adhesive interactions between hematopoietic progenitors expressing VLA-4 [Hemler et al., *Immunol. Rev.*, 114:45–65 (1990); Williams et al., *Nature*, 352:438–441 (1991); Roldan et al., *J. Exp. Med.*, 175:1739–1747 (1992); Sawada et al., *J. Immunol.*, 149:3517–3524 (1992); Wadsworth et al., *J. Immunol.*, 150:847–857 (1993)] and their ECM microenvironment play a critical role in precursor maturation and differentiation. Thus, CS-1 peptides have been shown to inhibit (i) attachment of murine hematopoietic stem cells to ECM derived from bone marrow stroma [Williams et al., *Nature*, 352:438–441 (1991)], (ii) immunoglobulin secretion by bone marrow-derived B cell progenitors [Roldan et al., *J. Exp. Med.*, 175:1739–1747 (1992)], (iii) bursal and postbursal development of chicken B cells [Palojoki et al., *Eur. J. Immunol.*, 23:721–726 (1993)], and (iv) thymocyte adhesion and differentiation induced by thymic stromal cell monolayers [Utsumi et al., *Proc. Natl. Acad. Sci. USA*, 88:5685–5689 (1991); Sawada et al., *J. Immunol.*, 149:3517–3524 (1992)]. VLA-4/CS-1 may also be involved in embryonic development, because CS-1 peptides have been shown to interfere with migration of avian neural crest cells [Dufour et al., *EMBO J.*, 7:2661–2671 (1988)].

In addition to VCAM-1, FN and CS-1 have also been implicated in the pathology of rheumatoid arthritis (RA) [Laffon et al., *J. Clin. Invest.*, 88:546–552 (1992)]. A role for the CS-1 splicing variant of FN has been established in mediating migration of inflammatory cells such as eosinophils across endothelial cell monolayers of VLA-4-expressing leukocytes [Kuijpers et al., *J. Exp. Med.*, 178:279–284 (1993)].

The vast body of work suggesting that VLA-4 plays a role in leukocyte trafficking and inflammation has been largely confirmed by in vivo studies using anti-VLA-4 antibodies in various animal models. Essentially, the skin, brain, kidney, lung and gut are targets of a wide variety of VLA-4-dependent inflammatory reactions mostly resulting from recruitment of mononuclear leukocytes and eosinophils.

More specifically, these in vivo studies are as follows: contact hypersensitivity (CH) and delayed type hypersensitivity (DTH) in the mouse and rat [Ferguson et al., *Proc. Natl. Acad. Sci. USA*, 88:8072–8076 (1991); Issekutz, *Cell Immunol.*, 138:300–312 (1991); Issekutz, *J. Immunol.*, 147:4178–4184 (1991); Elices et al., *Clin. Exp. Rheumatol.*, 11:S77–80 (1993); Ferguson et al., *Proc. Natl. Acad. Sci. USA*, 88:8072–8076 (1991); Chisholm, et al., *Eur. J. Immunol.*, 23:682–688 (1993)]; experimental autoimmune encephalomyelitis (EAE) in the mouse and rat [Yednock et al., *Nature*, 356:63–66 (1992); Baron et al., *J. Exp. Med.*, 177:57–68 (1993)]; nephrotoxic nephritis in the rat [Mulligan et al., *J. Clin. Invest.*, 91:577–587 (1993)]; passive cutaneous anaphylaxis in the guinea pig [Weg et al., *J. Exp. Med.*, 177:561–566 (1993)]; immune complex-induced lung injury in the rat [Mulligan et al., *J. Immunol.*, 150:2401–2406 (1993); Mulligan et al., *J. Immunol.*, 150:2407–2417 (1993)], spontaneous colitis in the monkey [Poldolsky et al., *J. Clin. Invest.*, 92:372–380 (1993)] and asthma in sheep [Lobb, WO 92/13798 published Jul. 22, 1993].

Thus, a preliminary conclusion from in vivo results is that VLA-4 contributes to inflammatory responses that emulate chronic conditions in humans. In an in vivo model of murine contact hypersensitivity, the CS-1 peptide partially inhibited recruitment of T lymphocytes to skin inflammatory sites [Ferguson et al., *Proc. Natl. Acad. Sci. USA*, 88:8072–8076 (1991)]. Because the Arg-Gly-Asp peptide from the cell adhesion domain of FN was also inhibitory in this animal model, the authors concluded that emigration of immune T cells to sites of antigenic challenge in the tissue could be facilitated by the interaction of leukocyte integrins with ECM proteins such as FN [Ferguson et al., *Proc. Natl. Acad. Sci. USA*, 88:8072–8076 (1991)].

In a more recent study, Elices and coworkers [Elices et al., *Clin. Exp. Rheumatol.*, 11:S77–80 (1993)] were unable to reproduce inhibition of contact hypersensitivity with the native CS-1 peptide. Instead, they found that the CS-1 peptide was rapidly cleared from blood circulation by proteolytic degradation.

The role of VIA-4 and the CS-1 peptide in various chronic and acute immunoinflammatory disease states having been established, it would be of importance if compounds could be found that inhibit the VLA-4-lymphocyte interaction and were other than anti-VLA-4 antibodies that can themselves induce an immune response on repeated administration or the CS-1 peptide that is large and costly to make, and also is subject to rapid degradation. The disclosure that follows describes such small molecules that are more potent than is CS-1 itself.

BRIEF SUMMARY OF THE INVENTION

The present invention contemplates CS-1 peptidomimetic inhibitor peptides, their compositions and methods (processes) for using those inhibitor peptides.

A contemplated peptide corresponds in sequence to formula I

X-Leu-Asp-Z             I wherein

X is a group amide-linked to the nitrogen atom of the Leu α-amine. The X group has a ring structure bonded to the carbonyl carbon of the amide-linkage by a spacer having a length of zero to about two methylene groups. The length of X, including the spacer and carbonyl carbon, is about that of a 3-quinolinecarbonyl group or smaller. The ring structure is a 5- and 6-membered ring or a fused 6,6- or 6,5-membered ring.

Z is selected from the group consisting of:
  (a) Xaa-NCy$^1$ where Xaa is Val, Ile, Leu or an aromatic amino acid residue; i.e., a residue having a side chain that contains one or two fused aromatic rings, and NCy$^1$ is a cyclic ring-containing group having a ring nitrogen atom that forms an amide bond with the α-carboxyl group of Xaa, and whose cyclic ring contains 5- or 6-atoms including said ring nitrogen atom;
  (b) NCy$^2$ where the depicted nitrogen is an amine substituent of a cyclic group whose depicted nitrogen atom forms an amide bond with the α-carboxyl group of the Asp, and which amine substituent is bonded to a 6- or 7-membered ring or to a fused 6,6- or 6,7-membered lactam ring system in which the ring bearing the amine substituent is saturated and contains the amine substituent α to the carbonyl group of the lactam; and
  (c) a Pro-NH$_2$ residue, or a peptide up to three residues in length having the sequence Pro-Ser or Pro-Ser-Thr in which the nitrogen of the Pro-NH$_2$ residue or peptide is peptide-bonded to the α-carboxyl group of the Asp.

A peptide of formula I, and formulas II and III hereinafter, is water-soluble and inhibits the binding of Jurkat cells (ATCC TIB 152) to a solid phase-bound peptide of SEQ ID NO:1 in an in vitro assay in an aqueous buffer at a pH value of 7.2–7.4 to an extent that is about 10- to about 1000-fold better than the inhibition in the binding exhibited by a peptide of SEQ ID NO:3.

In a more preferred embodiment, the X group has the formula Ar—Y—C(O)— and the peptide corresponds in sequence to formula II, below, Ar—Y—C(O)-Leu-Asp-Xaa-NCy$^1$   II wherein Ar is a pyrazolyl, phenyl, pyridyl, or 3-quinolinyl group;

Y is a spacer that is absent, —CH$_2$—, —CH(NH)—, —O— or —NH—;

or Ar—Y—C(O)— together with the nitrogen atom of said Leu forms a phthalimido, a 1,2,3,4-tetrahydroquinazoline-2,4-dione-3-yl or a 5-phenyldantoin-3-yl group, and Ar—Y—C(O)— has a length of about 3-quinolinecarbonyl or less.

Xaa is an aromatic amino acid residue; i.e., an amino acid residue having an aromatic side chain.

NCy$^1$ is an amine-containing 5- or 6-membered cyclic ring group whose depicted nitrogen atom is within the ring and forms an amide bond with α-carboxyl of Xaa, as discussed before.

Ar—Y—C(O)— is most preferably phenylacetyl, so that in most preferred practice, a contemplated peptide corresponds in sequence to formula III, below, N-phenylacetyl-Leu-Asp-Phe-NCy$^3$   III wherein NCy$^3$ is a most preferred NCy$^1$ group that is selected from the group consisting of morpholinamido, D-2-(carboxamide)pyrrolidinamido, piperidinamido, piperazinamido, pyrrolidinamido and 4-hydroxypiperidinamido groups.

A composition containing an above inhibitor peptide is also contemplated. Such a composition contains the peptide dissolved or dispersed in a pharmaceutically acceptable diluent that is preferably aqueous. The peptide is present in the composition in an inflammation-reducing amount. That amount is also sometimes referred to herein as a CS-1/VLA-4 binding inhibiting amount. An above-discussed more preferred or most preferred peptide is utilized in a more preferred or most preferred composition.

A process for treating fibronectin CS-1/VLA-4-mediated inflammation is also contemplated. That process comprises administering to a mammal having that inflammation or otherwise in need of such a treatment as for prophylactic purposes, an inflammation-reducing amount of a before-described inhibitor peptide. Use of a more preferred or most preferred inhibitor peptide is more or most preferred in this process.

All peptide formulas or sequences shown herein are written from left to right and in the direction from amino-terminus to carboxy-terminus. The abbreviations used herein for derivatives and residues of the twenty natural amino acids are reproduced in the following Table of Correspondence:

TABLE OF CORRESPONDENCE

| Abbreviation | | |
| --- | --- | --- |
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

The present invention has several benefits and advantages.

One salient benefit is that an inhibitor peptide contemplated here is more potent in inhibiting the VLA-4/CS-1 binding interaction than CS-1 itself.

Another benefit of the invention is that exemplary inhibitor peptides have been shown to be effective in reducing various exemplary immunoinflammation disease states in host mammals.

An advantage of the invention is that no adverse toxicity has been observed at in vivo concentrations of up to 600 mg/kg/day in a host laboratory mammal.

Another advantage of the invention is that a contemplated inhibitor peptide is a relatively small molecule that is easily prepared in high yield and purity.

Still further benefits and advantages of the invention will become apparent to the skilled worker from the disclosure that follows.

BRIEF DESCRIPTION OF THE DRAWINGS

In the drawings forming a portion of this disclosure:

FIG. 4 shown in two panels as FIG. 4A

FIG. 4B shows results obtained for the percent change in lung resistance ($L_R$) from the same study, with data being presented as in FIG. 4A. The ordinate is in units of percent change from the original lung resistance value, whereas the abscissa is in hours.

DETAILED DESCRIPTION OF THE INVENTION

Figure 1:
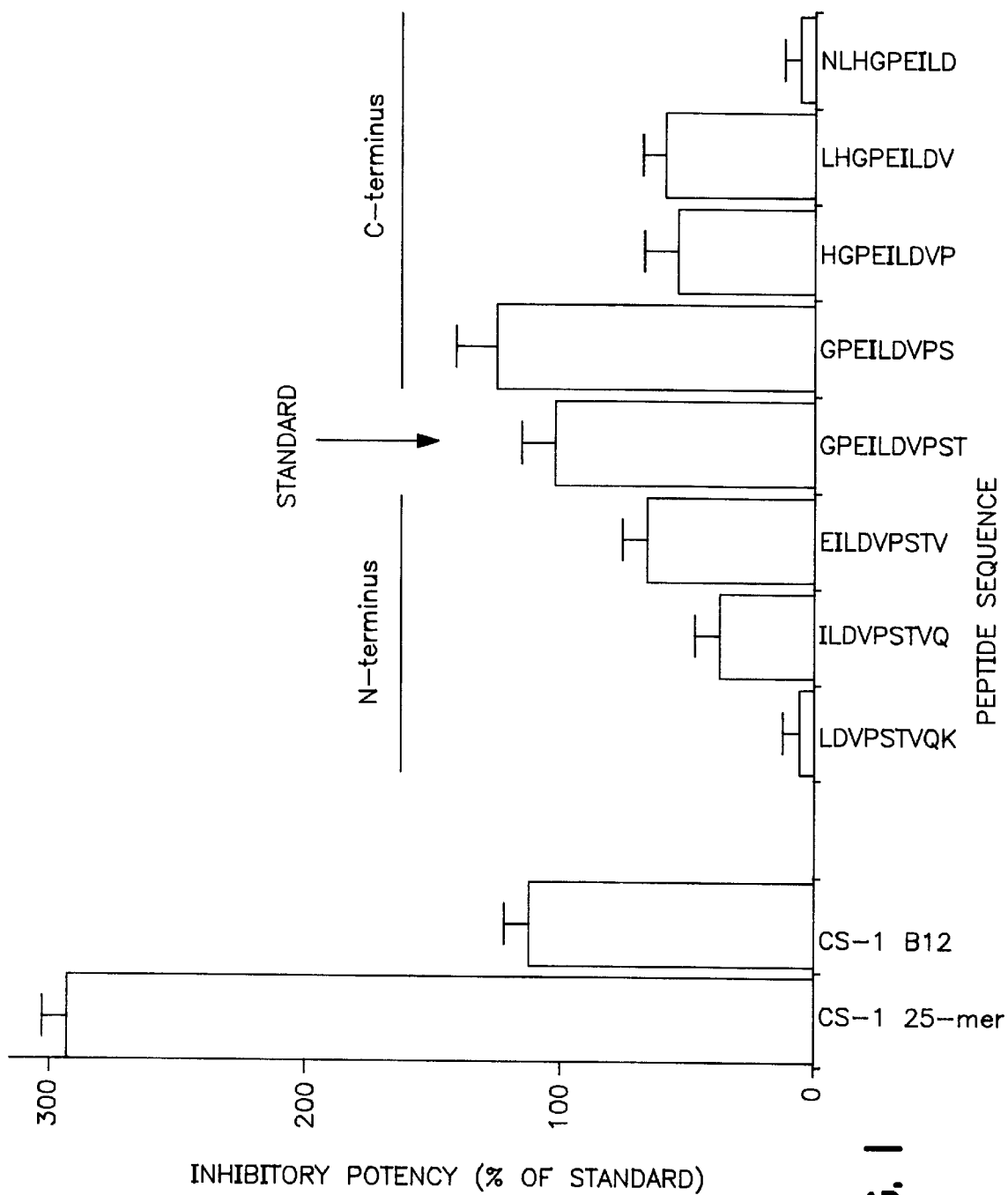
FIG. 1 is a graph illustrating the in vitro binding inhibition of VLA-4-bearing Jurkat cells to the solid phase-bound CS-1 peptide (SEQ ID NO:1) by that peptide itself and shorter peptides having portions of the CS-1 peptide sequence. Data are shown as percentages relative to the indicated "Standard" (SEQ ID NO:3). Data for peptides with deletions at the "IN-terminus" of peptide B12 (SEQ ID NO:2) are shown to the left of the Standard, and data for peptides with deletions at the "C-terminus" of peptide B12 are shown to the right of the standard. Peptide sequences are in single letter code.

The present invention contemplates an inhibitor peptide, a composition containing such a peptide, and a process of using such a peptide. A contemplated peptide inhibits binding between the CS-1 peptide of fibronectin and the inflammatory cell VLA-4 surface receptor, and is therefore sometimes referred to herein as an inhibitor peptide.

A. Peptides

A contemplated peptide can be viewed as a mimic of the whole fibronectin molecule, or at least the 25-residue (25-mer) CS-1 portion of fibronectin (SEQ ID NO:1) that binds to the VLA-4 receptor. As will be seen from the discussion that follows, a contemplated peptide binds to the VLA-4 receptor even more tightly than does the CS-1 25-mer peptide present in fibronectin.

Broadly, a contemplated inhibitor peptide can be defined as having a structure corresponding to formula I, below

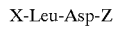   I wherein

X is a group amide-linked to the nitrogen atom of Leu, the group having a ring structure bonded to the carbonyl carbon of the amide-linkage by a spacer having a length of zero to about two methylene groups. The length of X, including the spacer and carbonyl carbon, is about that of a 3-quinolinecarbonyl group or smaller. The ring structure is a 5- and 6-membered ring or a fused 6,6- or 6,5-membered ring; and Z is selected from the group consisting of
  (a) Xaa-NCy$^1$ where Xaa is Val, Ile, Leu or an amino acid residue having a side chain that contains one or two fused aromatic rings and NCy$^1$ is a cyclic ring-containing group having a ring nitrogen atom that forms an amide bond with the α-carboxyl group of Xaa, and whose cyclic ring contains 5- or 6-atoms including said ring nitrogen atom;
  (b) NCy$^2$, where the depicted nitrogen is an amine substituent of a cyclic group whose depicted nitrogen atom forms an amide bond with the α-carboxyl group of the Asp residue, and which amine substituent is bonded to a 6- or 7-membered ring or to a fused 6,6- or 6,7-membered lactam ring system in which the ring bearing the amine substituent is saturated and contains the amine substituent α to the carbonyl group of the lactam; and
  (c) a Pro-NH$_2$ residue, or a peptide up to three residues in length having the sequence Pro-Ser or Pro-Ser-Thr in which the nitrogen of the Pro-NH$_2$ residue or peptide is peptide-bonded to the α-carboxyl group of said Asp.

A peptide of formula I, as well as formulas II and III below, is water-soluble and inhibits the binding of Jurkat cells (ATCC TIB 152) to a solid phase-bound peptide of SEQ ID NO:1 in an in vitro assay in an aqueous buffer at a pH value of 7.2–7.4 to an extent that is about 10- to about 1000-fold better than the inhibition in said binding exhibited by a peptide of SEQ ID NO:3.

Examining formula I, it is seen that at least Leu and Asp of the CS-1 (SEQ ID NO:1) and B12 (SEQ ID NO:2) fibronectin peptides are present. Aside from that two residue sequence, the sequence/structure of a contemplated inhibitor peptide and the CS-1 or B12 portions are quite different.

Thus, whereas there is an iso-leucine (Ile;I) peptide-(amide-) bonded to the α-amine group of the Leu residue in CS-1 and the native protein, a cyclic ring structure-containing group or moiety is amide-bonded to the nitrogen atom of that Leu residue α-amino group via a carboxyl contributed by the cyclic ring structure-containing group. That amide bond can be present as part of a carboxamide-[—C(O)—NH—], urethane-[—O—C(O)NH—] or urea [—NH—C(O)NH—] containing spacer group that links the cyclic ring structure-containing group to the Leu residue.

The cyclic ring structure broadly can be any 5- or 6-membered ring that is saturated or contains ethylenic unsaturation. The ring structure can contain one or more atoms other than carbon such as nitrogen, oxygen or sulfur. The ring structure can also be a fused ring system where two 6-membered rings are fused (6,6-) or where a 6-membered ring is fused to a 5-membered ring (6,5-membered). The ring of the cyclic ring structure is preferably aromatic.

Exemplary ring structures include tetrahydrofuranyl, tetrahydropyranyl, cyclopentyl, cyclohexyl, phenyl, pyridyl, pyrimidinyl, pyrazinyl, pyrazolyl, pyrrolidyl, furanyl, piperidinyl, naphthyl, quinolinyl, decalinyl, quinazolinyl, imidazyl, thiophenyl, and the like. Of the cyclic ring structures, phenyl and pyridyl are particularly preferred.

A cyclic ring structure can be bonded directly to the carbonyl group [—C(O)—] of the amide bond to the Leu residue. That ring can also be spaced away from the carbonyl group by up to about the length of two methylene (—CH$_2$—) groups or an ethylene group (—CH$_2$—CH$_2$—).

The Van der Waals radius a methylene group (about 2.0 Å) is slightly longer than that of an oxy group (—O—; about 1.40 Å) or an imino group (—NH—; about 1.50 Å). There is sufficient similarity between the sizes of methylene, oxy and imino so that a spacer group containing a —CH$_2$—O—, —CH$_2$—NH—, —NH—NH—, or —O—NH— are of similar lengths and are within the length of an ethylene group, —CH$_2$—CH$_2$—. A similar result obtains if bond lengths (distances) are used. Contemplated spacers include —HC (CH$_3$)—CH$_2$—, —CH$_2$—CH$_2$—, —NH—O—, —HN—NH—, —CH$_2$—O— and —CH$_2$—NH—, and are preferably free of unsaturation.

Using a phenyl ring as an exemplary aromatic ring structure, it is seen that the contemplated X groups include 3-methyl-3-phenylpropionyl, 3-phenylpropionyl, phenylhydroxaminocarbonyl [Ph—NH—O—C(O)—], phenylhydrazidecarbonyl [Ph—NH—NH—C(O)—], benzyloxycarbonyl [Ph—CH$_2$—O—C(O)—], phenoxyacetyl [Ph—O—CH$_2$—C(O)—], benzylaminocarbonyl [Ph—CH$_2$—NH—C (O)—], and anilinoacetyl [Ph—NH—CH$_2$—C(O)—], where "Ph" is a phenyl group.

Thus, it is contemplated that a before-described ring structure be bonded to the carbonyl carbon of the Leu-linked amide group by a spacer having a length of zero methylene groups (a direct bond), one or two methylene groups. Put differently, the spacer has the length of about an ethylene group or less.

A phenylacetyl, phenoxycarbonyl or anilinocarbonyl group bonded to the nitrogen of the Leu α-amino group contains a spacer having the length of about one methylene group. Phenyl(benzoyl), 1- or 2-naphthyl (1- or 2-naphthalenecarbonyl), 2-, 3- or 4-pyridyl (2-, 3- or 4-pyridinecarbonyl), 2- or 3-thiophenyl (2- or 3-thienyl; 2- or 3-thiophencarbonyl) and 2- or 3-furanyl (2- or 3-furancarbonyl) ring structures are bonded directly to the amide carbonyl carbon and therefore define an X group that utilizes a spacer having a length of zero methylene groups. A spacer having a length of about two methylene groups is provided by an X group that is carbobenzyloxy [Ph—CH$_2$—O— C(O)—], carbobenzylamino [Ph—CH$_2$—NH—C (O)—], carbophenoxymethylene [Ph—O—CH$_2$—C(O)—]) and the like groups.

A contemplated 5- or 6-membered ring structure can also be substituted with a C$_1$–C$_2$ alkyl or hydroxyl group. Exemplary substituted ring structures using a phenyl ring as illustrative thus include 2-, 3- or 4-ethylphenyl, 2,6-, 3,4- or 2,3-dimethylphenyl, 2-, 3- or 4-hydroxyphenyl, 2,6-, 2,4-, 3,4- and 3,5-dihydroxyphenyl, and the like.

The ring structure of the X substituent is thought to act in a contemplated inhibitor in some way to fit the inhibitor peptide into the binding pocket of the VLA-4 receptor to position the Leu and Asp groups into a proper configuration. Because of that presumed role in fitting the peptide into its receptor, there are some size constraints upon the ring structure-containing and spacer portions of X, in addition to those noted before as to the spacer group length. Thus, from the carbonyl-containing carbon of the amide bond to Leu, through the end of ring structure or its substituent furthest from the carbonyl group, the total length of the spacer plus ring structure-containing portion of X is about the size of a 3-quinolinecarbonyl group or smaller.

Inasmuch as a 3-quinolinecarbonyl group is the longest contemplated ring structure-containing X substituent, a 3-quinolinecarbonyl group is free from the above-discussed substituents that add to its length.

The length of a given X substituent can be readily determined. For example, one can use space-filling models to build exemplary cyclic ring structure-containing X groups and then compare the relative sizes of the prepared models. One can also use published bond lengths and bond angles to prepare a two-dimensional depiction of the sizes. Computer graphics programs are also well-known and available that can be used to prepare exemplary model X groups for length comparison to 3-quinolinoyl.

The X substituent, including the spacer, cyclic ring structure, the carbonyl group and the α-amino nitrogen atom of Leu can also together form an aromatic ring-substituted cyclic imido group. Exemplary of such cyclic imido groups are phthalimido, which is preferred, each of 2,3- and 3,4-pyridinedicarboximido, homophthalimido and 1,2,3,4-tetrahydroquinazoline-2,4-dione-3-yl groups in which the aromatic ring and cyclic imido group are fused together.

In another exemplary compound, the leucine nitrogen atom is an imido nitrogen atom within the ring of a 5-phenylhydantoin-3-yl group so that the aromatic phenyl ring is a substituent of a cyclic spacer and is spaced about one methylene away from the carbonyl group linked to the Leu residue. A similarly structured imido nitrogen-containing X group is present in a 2-phenylsuccinimido group formed on the Leu nitrogen atom.

The cyclic imido- and hydantoin-containing portions of the above-discussed X groups can thus be viewed as specialized spacer groups that limit the conformational degrees of freedom of the ring structures. Thus, for example, whereas the carbonyl, methylene and phenyl portions of a phenylacetyl group are each free to assume one or more of several conformations, a phthalimido X group can only spin about the axis of the leucine nitrogen-methine bond.

It is noted that although the X substituent must contain a cyclic ring structure that can be substituted as discussed before, that X substituent can also include a further substituent on other than the ring structure. When a further substituent is present, X preferably is an amino acid residue having a cyclic ring side chain that therefore includes a primary or secondary amine. Here, X is preferably a prolyl, phenylalanyl, tyrosinyl or phenylglycyl residue, the nitrogen atom of whose α-amino group is bonded to the further substituent.

That further substituent can be one amino acid residue through the remainder of the CS-1 polypeptide sequence toward the N-terminus thereof, with the sequence of that polypeptide beginning at the isoleucine of position 19 from the N-terminus of SEQ ID NO:1. A single residue or 18 separate amino acid residue substituent sequences are thereby defined.

Another exemplary further substituent linked via an amine group of X is biotin. In a particular example, biotin amide-bonded to ε-aminocaproic acid was amide-bonded to the α-amine of a phenylalanine (Phe) as an X group. The resulting compound contained the biotin fused ring amide-linked to the Phe X group via a chain of twelve atoms.

It should also be understood that an X group amino acid residue having a cyclic ring side chain can also be free of substituent groups. The nitrogen atom of the α-amine of such a residue can also be acylated as with a $C_1$–$C_6$ acyl group such as formyl, acetyl, iso-butyryl, or hexanoyl group. A $C_1$–$C_6$ acyl group bonded to the nitrogen of an α-amine group forms an amide bond at that nitrogen atom and provides no ionic charge to the peptide at a pH value of 7.2–7.4 as compared to the positive charge provided by an unsubstituted free α-amine.

The Z group of formula I can be one of three types of groups. The Z group in one embodiment (A) is a hydrophobic amino acid residue Xaa peptide-bonded to the Asp carboxyl and linked to a cyclic ring-containing group $NCy^1$ that has a ring nitrogen atom (the N of $NCy^1$) that forms an amide bond with the α-carboxyl group of Xaa. The cyclic ring of $NCy^1$ contains 5- or 6-atoms, including the depicted nitrogen atom (N of $NCy^1$). Contemplated hydrophobic amino acid residues are those having aliphatic side chains such as valine, leucine and isoleucine. Xaa more preferably contains a hydrophobic aromatic amino acid residue; i.e., Xaa is an amino acid residue having an aromatic side chain that contains one or two fused aromatic rings. Exemplary of such aromatic amino acids are phenylalanine, tyrosine and tryptophan that are naturally occurring (genetically encoded) as well as phenylglycine, homophenylalanine, p-nitrophenylalanine, thiophenylglycine (thienylglycine), and the like.

Exemplary $NCy^1$ groups include morpholinyl, piperidinyl, piperazinyl, pyrrolidinyl, pyrazolyl, pyrazolinyl, oxazolidinyl and the like as their respective amides. A $NCy^1$ cyclic ring can also be substituted with one or two substituent groups selected from the group consisting of carboxyl, carboxamide, hydroxyl, hydroxymethyl, and $C_1$–$C_4$ alkyl. Carboxyl substitution at the 2-position of a pyrrolidine provides the amino acid proline, whose D- and L-forms are both contemplated herein. D-Prolyl (sometimes shown in bold face lower case single letter amino acid code as "p" or as D-Pro) is particularly preferred as its amido derivative (D-Pro-$NH_2$) as are morpholinyl, piperidyl, piperazinyl and 4-hydroxypiperidyl. Exemplary $C_1$–$C_4$ alkyl groups include methyl, ethyl, iso-propyl, n-butyl and t-butyl.

Thus, in those embodiments where Z is Xaa-$NCy^1$, Xaa is a specified amino acid residue whose amine group forms an amide (peptide) bond with the α-carboxyl of the depicted Asp residue, and whose carboxyl group forms an amide bond with a nitrogen atom present within the 5- or 6-membered ring of $NCy^1$.

In another embodiment, B, Z is $NCy^2$ where the depicted nitrogen atom (N of $NCy^2$) is an amine substituent of a cyclic group ($Cy^2$) whose substituent nitrogen atom forms an amide bond with the α-carboxyl of the depicted Asp residue. That amine substituent is bonded to a cyclic group that is (i) a 6- or 7-membered ring or (ii) a fused 6,6- or 6,7-membered lactam ring system in which the ring bearing the amine substituent is saturated (free of ethylenic unsaturation) and contains the amine substituent α to the carboxyl group of the lactam.

Here, the nitrogen atom that links the ring system to the remainder of the peptide is a substituent of a cyclic ring structure rather than being a ring atom as in $NCy^1$. In addition, the rings of which that nitrogen can be a substituent are of two types, 6- or 7-membered rings or 6,6- or 6,7-membered fused ring systems, one of which rings is a lactam. In either situation, there is no Xaa amino acid residue in this embodiment.

Exemplary amine substituent-containing 6- and 7-membered ring $NCy^2$ groups of this type include benzylamine, phenethylamine, 2-(N-morpholinyl)ethylamine, N-[1-(carboxamidomethyl)-caprolactam-3-yl]amine, N-(caprolactam-3-yl)amine, and N-(valerolactam-3-yl)amine groups that form the corresponding amides with the α-carboxyl of Asp. Exemplary amino-substituted 6,6- and 6,7-fused ring lactam-containing $NCy^2$ groups include N-[1-(2-N-morpholinylethyl)-2-oxo-tetrahydroquinolin-3-yl]amine, N-(2-oxo-tetrahydroquinolin-3-yl)amine and the 6,7-fused ring tricyclic compound shown at footnote 7 of Table 1 groups that form corresponding amides with the α-carboxyl of Asp.

In the third embodiment, C, Z is the C-amide residue Pro-$NH_2$ or a peptide up to three residues in length having the sequences Pro-Ser or Pro-Ser-Thr.

When a contemplated peptide contains five or fewer amino acid residues, it is preferred that the only residue bearing an ionic charge at pH 7.2–7.4 be the illustrated aspartic acid residue of formula I or any other formula herein. Such a peptide is thus preferably free of N-terminal amino groups or C-terminal carboxyl groups as well as being free of residues or substituents therebetween that are charged at that pH range. A peptide containing six or more residues can contain one or both termini that bear an ionic charge at pH 7.2–7.4 with no intervening charged side chains or substituents, except for the illustrated Asp residue, although it is preferred that each terminus and the whole peptide be free of ionic charge (neutral) at pH 7.2–7.4 except for the ionic charge provided by the illustrated Asp residue.

It has generally been found that once (i) the X group of formula I is occupied by an aromatic ring-containing moiety spaced adjacent to or within about one methylene group's distance from the carbonyl, (ii) Z is an aromatic amino acid, and (iii) $NCy^1$ is L- or D-proline amide or a 5- or 6-membered nitrogen-containing ring as discussed before, substantially any other substituent can be present linked to either peptide terminus without diminishing the inhibitory activity of a contemplated peptide, so long as the resulting peptide is water-soluble.

Thus, for example, the peptide of SEQ ID NO:5 having an N-terminal phenylacetyl group linked to the sequence Leu-Asp-Phe-Pro can further include a substituted tetraethylenediamine group amide-bonded to the Pro residue in which four phenylacetyl-Leu-Asp-Phe-Pro groups were amide-bonded to the tetraethylenediamine nitrogens and still exhibit VLA-4 binding inhibition that was about 210 times better than the standard 10-mer peptide of SEQ ID NO:3.

Similarly, the peptide PheLeuAspPhe-D-Pro-NH$_2$ contained a europium-containing chelate at its N-terminus bonded to the nitrogen atom of the N-terminal Phe. That peptide exhibited a binding inhibition about 120 times better than that of the peptide of SEQ ID NO:3.

Biotin linked to either the C- or N-termini has provided conflicting results. Thus, N-(biotinoyl-ε-aminocaproyl)-Phe-Leu-Asp-Phe-D-Pro-NH$_2$ was about 150-fold better as an inhibitor than was the standard 10-mer peptide of SEQ ID NO:3. On the other hand, the peptide phenylacetyl-Leu-Asp-Phe-D-Pro amide-bonded to one amine of a 1,6-hexanediamine linker group whose other amine was amide-bonded to the carboxyl of biotin exhibited substantially no inhibition of binding between VLA-4 and the standard 10-mer peptide of SEQ ID NO:3.

The peptide of SEQ ID NO:12, phenylacetyl-Leu-Asp-Phe-Pro-NH(CH$_2$)$_5$C(O)NHC$_{18}$H$_{37}$, would be predicted to be a good inhibitor. However, that peptide is not water-soluble and forms a turbid dispersion rather than a solution. That peptide exhibits a binding inhibition similar to that exhibited by the standard 10-mer peptide of SEQ ID NO:3.

Binding phenomena involving structure-function relations such as those contemplated herein are not completely understood, although a skilled worker can usually make accurate predictions as to desired potency of a predicted peptide once sufficient data are in hand as is discussed hereinafter. Indeed, substantially all of the compounds defined by formula I inhibit binding between the CS-1 peptide and the VLA-4 receptor. Nonetheless, because the substituents bonded directly to Leu and Asp of formula I can vary widely and affect binding inhibition to VLA-4, a contemplated inhibitor peptide is defined not only by its structure, but also by its potency as an inhibitor in a standard in vitro assay as compared to a standard, known, 10-mer peptide inhibitor, to include only those inhibitor peptides that inhibit binding by about one order of magnitude or more better than the known 10-mer inhibitor.

A contemplated inhibitor peptide thus inhibits the binding of inflammatory cells that contain the VLA-4 receptor [Jurkat cells (American Type Culture Collection, Rockville, Md. 20852, ATCC TIB 152)] to the solid phase-bound CS-1 peptide (SEQ ID NO:1) in an aqueous buffer at pH 7.2–7.4 to an extent that is about 10-fold to about 1000-fold better than that binding exhibited by the standard 10-mer peptide of SEQ ID NO:3 (GPEILDVPST in single letter code). More preferably that binding is inhibited by about 50- to about 1000-fold, and most preferably by about 100- to about 1000-fold.

Binding inhibition is measured here as a concentration of peptide that inhibits one-half the binding between a standard number of Jurkat cells and a standard amount of CS-1 peptide bound to the surface of a microtiter plate well. Those concentrations are conveniently expressed as IC$_{50}$ values, smaller numbers indicating a lower concentration required to inhibit 50 percent binding and therefore greater potency. Further specifics of this assay are provided hereinafter.

To recapitulate, a peptide of formula I inhibits binding between the CS-1 peptide region of fibronectin and the VLA-4 receptor. However, only those inhibitors that are at least ten-times better inhibitors than the peptide of SEQ ID NO:3 are contemplated here.

Still more preferred is a peptide of formula II, below,

Ar—Y—C(O)-Leu-Asp-Xaa-NCy$^1$                II wherein

Ar is a pyrazolyl, phenyl, pyridyl (2-, 3- or 4-), or 3-quinolinyl group;

Y is a spacer that is absent, —CH$_2$—, —CH(NH)—, —O— or —NH—;

or Ar—Y—C(O) together with the nitrogen atom of Leu forms a phthalimido, a 1,2,3,4-tetrahydroquinazoline-2,4-dione-3-yl or 5-phenylhydantoin-3-yl group, Ar—Y—C(O)— has a length of about 3-quinolinecarbonyl or less;

Xaa is an aromatic amino acid residue; i.e., an amino acid residue having an aromatic side chain, such as phenylalanine, tyrosine, tryptophan, homophenylalanine, nitrophenylalanine, thienylglycine and phenylglycine; and NCy$^1$ is an amine-containing 5- or 6-membered cyclic ring group whose depicted nitrogen atom, N of NCy$^1$, is within the ring and forms an amide bond with the α-carboxyl of Xaa, as was discussed before.

The water-soluble compounds of formula II thus far examined exhibit binding inhibitions of at least 10-fold better than that exhibited by the peptide of SEQ ID NO:3, and thus no in vitro assay is required for their complete definition, although that assay applies to all of the inhibitor peptides contemplated.

Of the above combinations, Ar—Y—C(O), a more preferred X group of formula I, is preferably benzoyl, phenylacetyl, 4-pyridinecarbonyl(isonicotinoyl), 3-pyridinecarbonyl(nicotinoyl), 3-pyridinacetyl, anilinocarbonyl, 3-quinolinoyl, pyrazolecarbonyl, tryptophyl and 3,4-dihydroxybenzoyl, with phenylacetyl (benzylcarbonyl) being most preferred, or Ar—Y—C(O) together with the leucine nitrogen atom form a phthalimido group. Xaa is preferably Phe, Tyr or Trp, with Phe being most preferred. NCy$^1$ is preferably an amount of a morpholinyl, 4-hydroxypiperidinyl, L- or D-prolinyl amide, pyrrolidinyl, piperazinyl, 3,4-dihydroxypyrrolidinyl and 2-(hydroxymethyl)pyrrolidinyl group, with amides of morpholinyl, D-prolinyl amide, piperidinyl, piperazinyl, pyrrolidinyl and 4-hydroxypiperidinyl groups being most preferred.

A most preferred peptide corresponds in sequence to a peptide of formula III, below,

Phenylacetyl-Leu-Asp-Phe-NCy$^3$                III wherein NCy$^3$ is a group of most preferred NCy$^1$ groups and is selected from the group consisting of morpholinamido, D-2-(carboxamido)pyrrolidinamido, piperidinamido, piperazinamido, pyrrolidinamido and 4-hydroxypiperidinamido groups.

Exemplary inhibitor peptides are listed in Table 1 below along with their binding inhibition potencies relative to the standard peptide of SEQ ID NO:3.

TABLE 1

RELATIVE PEPTIDE INHIBITION OF VLA-4 BINDING CS-1

| SEQ ID NO: | FORMULA[1] | | | | | | | X | Z[2] | | RELATIVE POTENCY[6] |
|---|---|---|---|---|---|---|---|---|---|---|---|
| | | X | L | D | F | Z | | phenylacetyl | morpholinamide | | 844 |
| | | X | L | D | F | p | | pyridine-4-carbonyl | amide | | 656 |
| | | X | L | D | Y | p | | phenylacetyl | amide | | 640 |
| | | X | L | D | F | Z | | phenylacetyl | 4-hydroxypiperidinamide | | 603 |
| | | X | L | D | F | Z | | phenylacetyl | piperazinamide | | 506 |
| | | X | L | D | F | p | | pyridine-3-acetyl | amide | | 469 |
| 4 | | X | L | D | Y | P | | phenylacetyl | amide | | 405 |
| | | X | L | D | Y | Z | | phenylacetyl | morpholinamide | | 313 |
| | | X | L | D | F | p | | phenylacetyl | amide | | 313 |
| | | X | L | D | L | Z | | phenylacetyl | morpholinamide | | 291 |
| | | X | L | D | F | Z | | phenylacetyl | pyrrolidinamide | | 250 |
| | | X | L | D | F | Z | | phenylacetyl | piperidinamide | | 231 |
| | | X | L | D | F | p | | anilinocarbonyl | amide | | 227 |
| 5 | | X | L | D | F | P | Z | phenylacetyl | peptide-substituted tetra-ethylenepentaamine[3] | | 209 |
| | | X | L | D | F | p | | pyridine-3-carbonyl | amide | | 201 |
| | | X | L | D | F | Z | | phenylacetyl | 3,4-dihydroxypyrrolidin-amide | | 194 |
| | | X | L | D | F | Z | | phenylacetyl | 2-(hydroxymethyl)prolin-amide | | 184 |
| | | X | L | D | W | p | | phenylacetyl | amide | | 184 |
| | B Z | F | L | D | F | p | | B = biotinoyl | Z = ε-amidocaproyl | amide | 150 |
| | | X | L | D | V | p | | phthalimido | amide | | 140 |
| | Z X | F | L | D | F | p | | ε-amidocaproyl[4] | Z = Europium label[4] | amide | 118 |
| | | X | L | D | V | p | | phenylacetyl | amide | | 106 |
| | | X | L | D | Z | | | phenylacetyl | N-[1-(carboxamidomethyl)-caprolactam-3-yl]amide | | 97 |
| | | X | L | D | J | p | | phenylacetyl | amide | J = homo-Phe[5] | 94 |
| | | X | L | D | F | Z | | 3,4-dihydroxyphenylacetyl | piperidinamide | | 81 |
| | | X | L | D | F | p | | benzoyl | amide | | 75 |
| | | X | L | D | V | p | | pyridine-3-carbonyl | amide | | 71 |
| | | X | L | D | J | p | | phenylacetyl | amide | J = Phenyl-Gly[5] | 61 |
| | | X | L | D | F | p | | 3-quinolinecarbonyl | amide | | 56 |
| | | X | L | D | F | p | | 1,2,3,4-tetrahydroquinazoline-2,4-dione-3-yl | amide | | 56 |
| | | X | L | D | Z | | | phenylacetyl | 6,7-fused ring Lactam[7] | | 50 |
| | | P | L | D | f | p | | free amine | amide | | 47 |
| | | X | L | D | Z | | | phenylacetyl | N-[(1-carboxamidomethyl)-2-oxo-tetrahydroquinolin-3-yl]amide | | 45 |
| 6 | X | F | L | D | L | Z | | GlcNAc—O—(CH$_2$)$_5$—C(O) | piperidinamide | | 41 |
| | | X | L | D | J | p | | phenylacetyl | amide | J = p-nitro-Phe[5] | 40 |
| 7 | | X | L | D | V | P | | benzoyl | amide | | 37 |
| | | F | L | D | F | p | | acetyl | amide | | 35 |
| | | X | L | D | F | p | | benzyloxycarbonyl | amide | | 34 |
| | | X | L | D | F | Z | | (5-phenyl)hydantoinyl | piperidinamide | | 34 |
| | | X | L | D | F | p | | pyrazolecarbonyl | amide | | 35 |
| | | F | L | D | F | p | | acetyl | amide | | 33 |
| | | X | L | D | Z | | | phenylacetyl | N-(2-oxo-tetratrahydro-quinolin-3-yl)amide | | 31 |
| | | X | L | D | Z | | | phenylacetyl | N-(caprolactam-3-yl)-amide | | 27 |
| | | X | L | D | F | Z | | phenylacetyl | propanolamide | | 25 |
| | | X | L | D | Y | Z | | 4-pyridinecarbonyl | piperidinamide | | 24 |
| | | X | L | D | Z | | | phenylacetyl | N-[1-(2-N-morpholinylethyl)-2-oxo-tetrahydroquinoline-3-yl]amide | | 20 |
| 8 | | X | L | D | V | P | | pivaloyl | amide | | 20 |
| | | X | L | D | V | p | | benzoyl | amide | | 20 |
| | | X | L | D | Z | | | phenylacetyl | benzylamide | | 19 |
| | | X | L | D | Z | | | phenylacetyl | phenethylamide | | 19 |
| | | X | J | D | F | p | | benzoyl | amide | J = cyclohexyl-Ala[5] | 17 |
| | | X | L | D | Z | | | phenylacetyl | N-D-(caprolactam-3-yl)amide | | 17 |
| | | X | L | D | S | p | | phenylacetyl | amide | | 17 |
| | | X | L | D | Y | Z | | phenylacetyl | t-butylester | | 15 |
| | | X | L | D | V | p | | phenylpropionyl | amide | | 14 |
| | | X | L | D | Z | | | phenylacetyl | N-(2-N-morpholinyl)ethyl-amide | | 13 |
| | | X | J | D | V | p | | benzoyl | amide | J = cyclohexyl-Ala[5] | 11 |
| | | F | L | D | V | p | | free amine | amide | | 10 |
| | | X | L | D | F | p | | 2-pyrazinecarbonyl | amide | | 9 |
| | | X | L | D | G | Z | | phenylacetyl | morpholinamide | | 9 |

TABLE 1-continued

RELATIVE PEPTIDE INHIBITION OF VLA-4 BINDING
CS-1

| SEQ ID NO: | FORMULA[1] | | | | | | | | | X | Z[2] | | RELATIVE POTENCY[6] |
|---|---|---|---|---|---|---|---|---|---|---|---|---|---|
| | X | L | D | V | p | | | | | 2,3-dimethylbenzoyl | amide | | 9 |
| | X | L | D | V | p | | | | | 3,4-dimethylbenzoyl | amide | | 8 |
| | X | L | D | V | p | | | | | pyridine-2-carbonyl | amide | | 8 |
| | X | L | D | Z | | | | | | phenylacetyl | Z = N-[1-(N-(cyclohexyl)-butyrolactam-3-yl]amide | | 7 |
| | X | L | D | Z | | | | | | phenylacetyl | N-(1-iso-butyl-2-oxo-tetrahydroquinolin-3-yl)amide | | 6 |
| | X | L | D | F | Z | | | | | benzyl | piperidinamide | | 6 |
| | f | L | D | V | p | | | | | free amine | amide | | 5 |
| | X | L | D | V | p | | | | | cyclohexanecarbonyl | amide | | 5 |
| | X | L | D | V | p | | | | | 2,6-dimethylbenzoyl | amide | | 5 |
| | X | L | D | F | p | | | | | 2-quinolinecarbonyl | amide | | 4 |
| | X | L | D | V | p | | | | | 3-methylvaleroyl | amide | | 3 |
| | X | L | D | Z | | | | | | phenylacetyl | N-(tetrahydroisoquinolin-3-yl)amide | | 3 |
| | p | L | D | F | p | | | | | free amine | amide | | 3 |
| | X | L | D | F | p | | | | | 8-quinolinesulfonyl | amide | | 3 |
| | X | L | D | F | Z | | | | | phenylacetyl | n-butylamide | | 3 |
| | X | L | D | V | p | | | | | 4-methylvaleroyl | amide | | 3 |
| | X | L | D | Y | | | | | | phenylacetyl | t-butyl ester | | 3 |
| | X | L | D | Z | | | | | | phenylacetyl | benzylhydrylamide | | 3 |
| | X | L | D | F | p | | | | | p-bromophenylacetyl | amide | | 3 |
| | I | L | D | F | p | | | | | free amine | amide | | 2 |
| 9 | X | L | D | F | P | Z | | | | phenylacetyl | decylamide | | 2 |
| 10 | I | L | D | V | P | I | L | D | V P | free amine | amide | | 2 |
| | X | J | D | F | p | | | | | benzylamide | amide | J = dicarboxy-Leu[5] | 2 |
| | X | L | D | V | p | | | | | cyclohexaneacetyl | amide | | 2 |
| | X | L | D | Z | | | | | | phenylacetyl | N'-t-Boc-hydrazide | | 2 |
| 11 | I | L | D | F | P | | | | | free amine | amide | | 2 |
| | X | L | D | V | p | | | | | 1-naphthoyl | amide | | 1 |
| | X | L | D | V | p | | | | | cyclohexanepropionyl | amide | | 1 |
| | X | L | D | Z | | | | | | phenylacetyl | N'-benzyl-N'-cyclopenane-carbonylhydrazide | | 1 |
| | F | J | D | F | p | | | | | free amine | amide | cyclohexyl-Ala[5] | 1 |
| | i | L | D | V | p | | | | | free amine | amide | | 1 |
| | I | L | D | V | p | | | | | free amine | amide | | 1 |
| | I | J | D | F | p | | | | | free amine | amide | cyclohexyl-Ala[5] | 1 |
| | X | L | D | V | p | | | | | cinnamoyl | amide | | 1 |
| 3 | G | P | E | I | L | D | V | P | S T | free amine | free acid | | 1 |
| 12 | X | L | D | F | P | Z | | | | phenylacetyl | HN(CH$_2$)$_5$C(O)NHC$_{18}$H$_{37}$ | | 1 |
| | X | L | D | F | | | | | | phenylacetyl | amide | | 1 |
| | X | L | D | F | Z | | | | | phenylacetyl | N-(4-decoyloxy)piperidin-amide | | 1 |
| | X | L | D | F | Z | | | | | phenylacetyl | N-(4-stearoyloxy)piperidin-amide | | 1 |
| | | L | D | V | | | | | | acetyl | amide | | 1 |
| | X | L | D | Z | | | | | | phenylacetyl | hydrazide | | 1 |
| | X | L | D | V | p | | | | | adamantanecarbonyl | amide | | 1 |
| | X | L | D | V | p | | | | | 2-naphthoyl | amide | | 1 |
| 13 | I | L | D | V | P | | | | | free amine | amide | | 1 |
| 14 | I | L | D | V | P | | | | | free amine | free acid | | 1 |
| | | L | D | F | | | | | | acetyl | amide | | <1 |
| | X | D | L | F | p | | | | | phenylacetyl | amide | | <1 |
| 15 | S | F | D | F | S | | | | | acetyl | amide | | <1 |
| | I | J | D | V | p | | | | | free amine | amide | J = cyclohexyl-Ala[5] | <1 |
| | X | L | D | F | p | | | | | 4-bromophenylsulfonyl | amide | | <1 |
| | | L | D | F | Z | | | | | free amine | piperidinamide | | 0 |
| | | J | D | F | Z | | | | | J = iso-butyloxycarbonyl | piperidinamide | | 0 |
| | X | L | D | Z | | | | | | phenylacetyl | N',N'-dibenzylhydrazide | | 0 |
| | X | L | D | Z | | | | | | phenylacetyl | N-(1,3-diphenylprop-2-yl)-amide | | 0 |
| | X | L | D | Z | | | | | | phenylacetyl | dibenzylamide | | 0 |
| | X | L | D | F | p | | | | | phenylsulfonyl | amide | | 0 |
| | | L | D | F | | | | | | free amine | amide | | 0 |

TABLE 1-continued

RELATIVE PEPTIDE INHIBITION OF VLA-4 BINDING CS-1

| SEQ ID NO: | FORMULA[1] | | | | | | X | Z[2] | | RELATIVE POTENCY[6] |
|---|---|---|---|---|---|---|---|---|---|---|
| | | L | D | V | | | free amine | amide | | 0 |
| | f | L | D | V | p | | free amine | free acid | | 0 |
| | X | L | D | F | p | Z | phenylacetyl | amide | linker arm-biotin[8] | 0 |

[1]A lower case letter in bold-faced type is used to designate a D-isomer of the L-amino acid residue designated in single letter code by the same capitol letter. Thus, p = D-proline; f = D-phenylalanine; i-D-isoleucine. The N-terminal α-amine is substituted as shown or indicated to be a "free amine".
[2]The state of the C-terminal carboxyl of Z as an "amide" (—$NH_2$) or "free acid" is noted as appropriate.
[3]Z is an amide formed between the C-terminal Pro carboxyl and a tetraethylenepentaamine containing four N-phenylacetyl-LDFP peptides amide-bonded thereto.
[4]Diethylenetriaminepentaacetatoeuropium (II) amide-bonded to Z.
[5]"Homo-Phe" = homophenylalanine; "phenyl-Gly" = phenylglycine; "p-nitro-Phe" = p-nitrophenylalanine; β-carboxy-Asp = β-carboxyaspartic acid; "cyclohexyl-Ala" = cyclohexylalanine; and "dicarboxy-Leu" = dicarboxyleucine.
[6]Relative activities of about one-tenth or less than that exhibited by the peptides of SEQ ID NO: 3 are assigned a potency activity of zero.
[7]

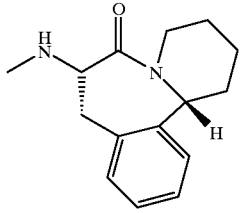

[8]Amide formed from 1,6-hexanediamine amide-bonded to biotin.

The data of Table 1 can be used to predict potency in binding inhibition for an unmade or another inhibitor peptide. Thus, one can examine the structures of Table 1 and use the observed relative inhibition potencies to calculate the relative contribution of individual residues or terminal groups. With such calculations in hand, one can then predict the potency of another contemplated peptide within a factor of about 5–10.

For example, comparing the inhibitions exhibited by N-phenylacetyl-Leu-Asp-Val-D-Pro-$NH_2$ and N-phenylacetyl-Leu-Asp-Phe-D-Pro-$NH_2$ one sees that replacement of Val by Phe provides an enhancement of inhibition by a factor of about 3. The differences between the otherwise similar pyridine-3-carbonyl derivatives is similarly about 3.

One could therefore predict that the two N-benzoyl derivatives of the peptides immediately above would similarly be about a factor of three different in their potencies. The data in Table 1 indicate that the observed difference is about a factor of 3.8, thereby verifying the prediction.

Carrying this useful but simplified procedure further, it can be calculated from peptides N-phenylacetyl-Leu-Asp-Phe-D-Pro-$NH_2$ and N-phenylacetyl-Leu-Asp-Phe-piperidinamide that D-Pro-$NH_2$ provides about 1.3-times greater activity than does piperidinamide. Comparing the activity of the latter peptide to that having a morpholinamide group, one calculates an enhancement of about 3.6-fold for a morpholineamide as compared to piperidinamide group. Comparing the peptides N-phenylacetyl-Leu-Asp-Tyr-morpholinamide and N-phenylacetyl-Leu-Asp-Tyr-D-Pro-$NH_2$, one finds an enhancement in activity of about a 2.05-fold for morpholinamide over D-Pro-$NH_2$. Using those two calculations, one can then calculate that a morpholinamide group provides about 7.4-times the enhancement of a piperidinamide group (2.05×3.6). That predicted enhancement is about 5.7-times greater than that found with the first two peptides (7.4/1.3), but within the range of the before-stated predictability.

The data of Table 1 also illustrate the unexpected enhancements in binding inhibition exhibited by an inhibitor peptide contemplated herein as compared to other peptides of the art. For example, the Leu-Asp-Val (LDV) peptide stated as being a minimal peptide required for binding of the VLA-4 receptor in WO 93/12809 exhibited a relative inhibitory binding activity of about 1 as the N-acetyl C-amide derivative and zero as the N-free amine C-amide as compared to the peptide of SEQ ID NO:3. Similar results were observed with Leu-Asp-Phe (LDF) that is not disclosed in that published application, but is an important core peptide here. Contrarily, when an X and Z group as defined herein are added to the termini of either peptide, enhancements in binding inhibition of about 1 to about 3 orders of magnitude were observed.

Figure 2:
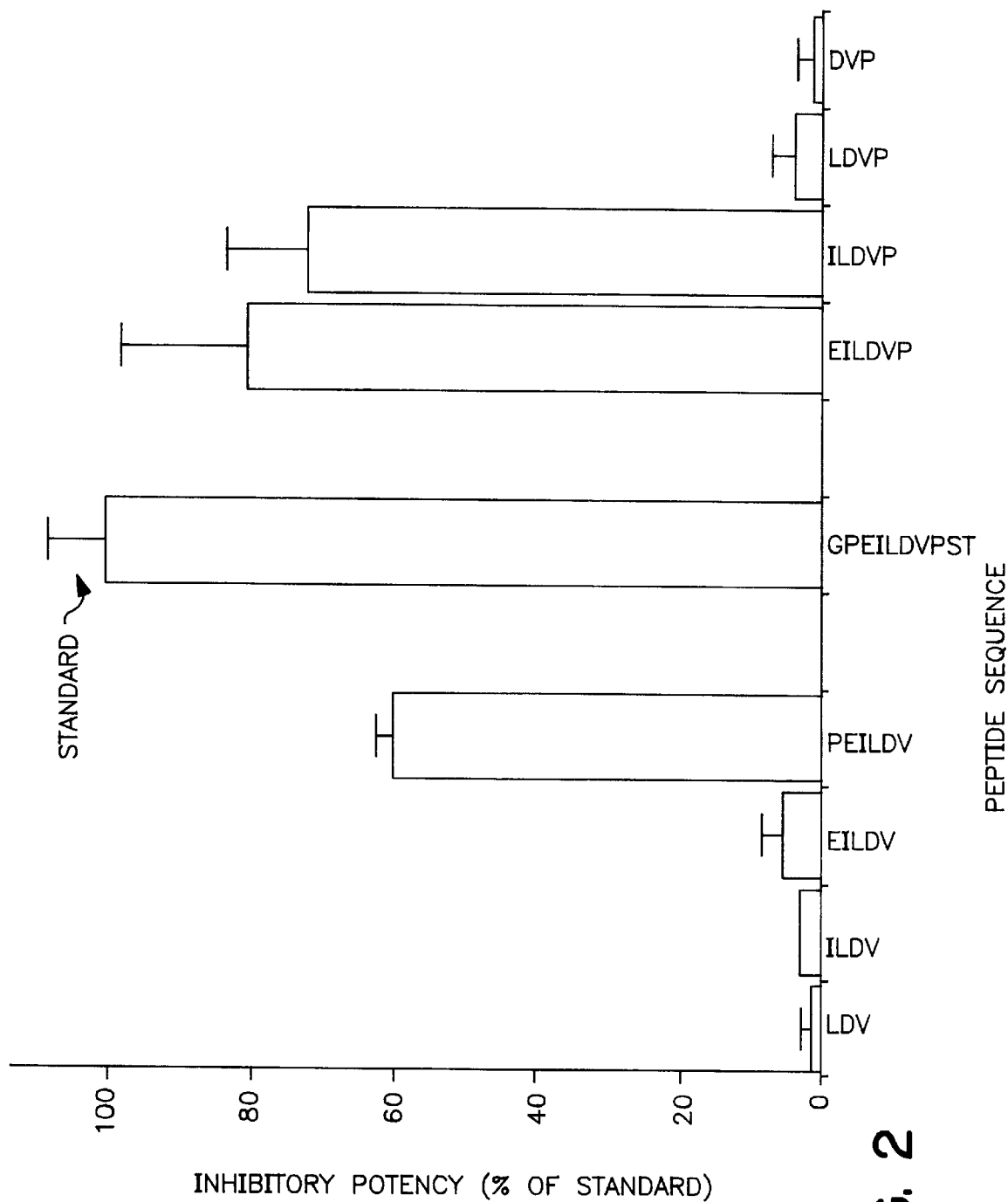
FIG. 2 is a graph with data obtained and expressed similarly to those of FIG. 1. Here, binding inhibition by further, still shorter deletion peptides, is illustrated.
Figure 3:
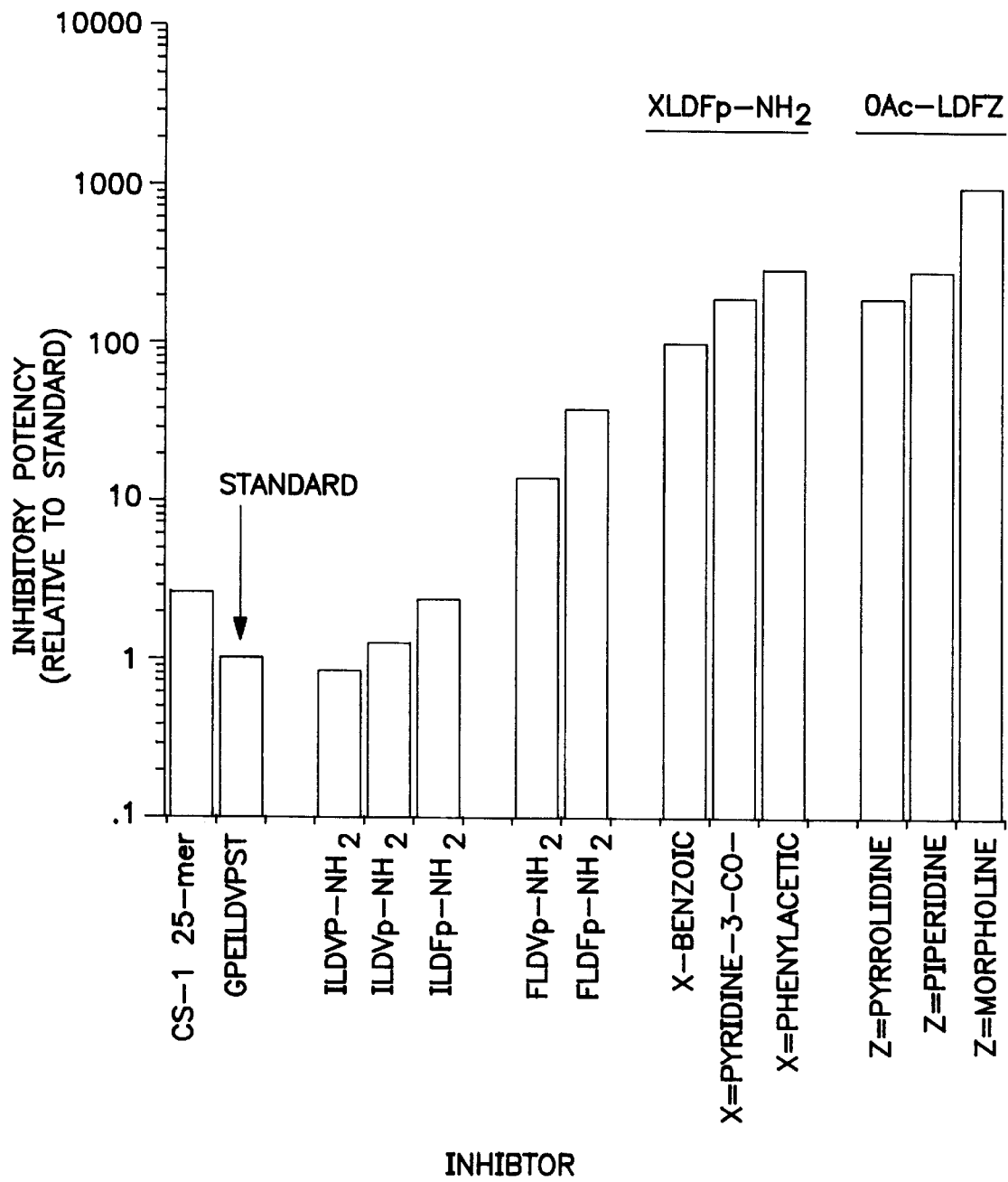
FIG. 3 is another graph of binding data obtained as discussed in FIG. 1. This graph utilizes an ordinate that is on a log scale. These data are arranged into five groups and are again shown relative to the indicated Standard peptide (SEQ ID NO:3), with D-proline being shown as "p". The data of the right-hand-most two groups illustrate the effects of three different X groups on a single indicated peptide and of three Z groups in which X is phenylacetyl (φAc) and Z is as shown, respectively.

The data shown in FIGS. 1, 2 and 3 also illustrate the unexpected binding inhibitions exhibited by contemplated peptides relative to other peptides of the art. The peptide sequences are shown using single letter code.

For example, FIG. 1 illustrates results of relative in vitro binding inhibition studies carried out using the CS-1 (SEQ ID NO:1) peptide, B12 portion of the CS-1 peptide (CS-1 B12; SEQ ID NO:2), the 10-mer peptide used as a standard above and elsewhere herein (SEQ ID NO:3) and several deletion analogues of the B12 peptide, each of which contained the Leu-Asp sequence. N-Terminal deletion analogues are shown to the left of the standard 10-mer, whereas C-terminal deletions are shown to the right of the 10-mer. As is seen, the CS-1 peptide is about three times more potent an inhibitor than is B12, the 10-mer or a 9-mer deletion analogue of the 10-mer. Those latter three peptides were all more potent than the other B12-related peptides.

The similarly obtained data of FIG. 2 illustrate binding inhibition results obtained using deletion analogues of the standard 10-mer peptide. Here, deletions made at both N- and C-termini are shown to the left of the standard 10-mer to isolate the Leu-Asp-Val sequence at the C-terminus, whereas those shown to the right of the standard 10-mer isolate the Asp-Val-Pro sequence. These peptides and those of FIG. 1 had free N-terminal amine groups and C-terminal carboxyl groups.

The data of FIG. 3 were similarly obtained, but are shown on a log scale so that all of the data could be accommodated. The data of FIG. 3 are shown in five groups, from left to right.

The first group show data for CS-1 peptide and the 10-mer standard. The next three bars shown data for a pentamer C-amide having the sequence including Leu-Asp-Val of the native CS-1 peptide, the enhanced effect of using D-proline instead of the native L-proline, and then the enhancement by use of phenylalanine and D-proline in place of valine and D-proline. The next two bars illustrate the further enhancement obtained over the three previous peptides obtained when a cyclic ring-containing X group, here phenylalanine as the free amine, was used to replace the isoleucine of the native sequence. The fourth group of bars illustrates the effects of three X groups of formula I as compared to the phenylalanine group, using the better peptide sequence of the two adjacent sequence [XLDFp-NH$_2$]. Phenylacetyl was used as an X group ($\phi$Ac) in the last three peptides where the D-proline Z group of formula I was varied using three cyclic amines (NCy$^1$). As is seen, use of a morpholinamide group as Z, along with phenylacetyl as X and phenylalanine as Xaa of formula I, provided the greatest potency in these studies.

Thus, the data of FIG. 3 show inhibitory potencies spanning about three orders of magnitude from the standard 10-mer and peptides of the art, through contemplated peptides that exhibit about a 10-fold enhancement in potency over that standard to those contemplated peptides exhibiting about a 50-fold to about 100-fold enhancement in potency and those exhibiting an enhancement in potency of up to about 1000-fold.

In addition to being more potent than the CS-1 or standard 10-mer peptides, a contemplated inhibitor peptide, particularly a peptide with non-naturally occurring terminal groups such as N-phenylacetyl and C-morpholinamide or D-Pro-NH$_2$, is relatively more stable in serum that is the CS-1 peptide. Thus, the inhibitor peptides N-phenylacetyl-Leu-Asp-Phe-morpholinamide and N-phenylacetyl-Leu-Asp-Phe-D-Pro-NH$_2$ exhibited no loss of potency after 24 hours in PBS at 7.2–7.4 that also contained 10 percent mouse or human serum. Contrarily, the CS-1 peptide lost its potency in less than one hour under the same conditions.

B. Syntheses

The contemplated inhibitors are peptides or peptide derivatives, and as such, can be readily synthesized using well known synthetic methods. Specific synthetic examples are provided hereinafter.

Solid phase synthesis was used for those materials having a C-terminal amino acid amide or free acid residue. Thus, the N-protected, C-terminal residue was linked to a solid support having a benzhydrylamine substituent. Fmoc amine blocking groups were used in these syntheses, although t-Boc, CBZ or other blocking groups can also be used with other solid supports. Upon deblocking the Fmoc group with piperidine, another residue was coupled. That coupling was followed by further deblocking, coupling, deblocking etc. steps until a solid phase-linked peptide of desired sequence was prepared. As appropriate to each peptide, an N-terminal X group was added after a final N-deblocking step or sometimes pre-coupled to the N-terminal residue. The desired peptide and any accompanying functional group protecting groups were removed from the solid support by reaction with trifluoroacetic acid (TFA). This procedure results in a C-amide-terminated peptide when a benzhydrylamine solid support is used.

Contemplated peptides can also be prepared using t-Boc N-protecting groups and another solid support, or a benzylamino-substituted solid support to which a p-hydroxymethylphenylcarboxyl (PAM) group is first reacted with the amine of the support to form a carboxamide. The hydroxyl group is then used to form an ester link to the first peptide and standard t-Boc synthetic technology is thereafter followed. Reaction of the completed, deprotected solid phase-linked peptide with ammonia provides the C-terminal amide peptide discussed before, whereas reaction with another amine such as morpholine or piperidine or other NCy$^1$ or NCy$^2$ amine provides a peptide whose C-terminal residue is amide-bonded to an NCy$^1$ or NCy$^2$ group. Reaction of a deprotected, PAM-linked peptide with hydroxide provides the corresponding C-terminal carboxyl group.

In other embodiments, liquid phase peptide syntheses were utilized. For example, morpholine or other NCy$^1$ or NCy$^2$ group was coupled in solution to a contemplated C-terminal, t-Boc-protected residue using a carbodiimide. The t-Boc protecting group was removed with acid, a further t-Boc-protected residue added, followed by deblockings and further additions. The N-terminal X group such as phenylacetic acid was added after the last t-Boc removal step and the synthesis was completed, except for deprotecting the Asp residue. That step was carried out by catalytic hydrogenation where a benzyl ester protecting group was used.

Regardless of the synthetic method used, an inhibitor peptide is typically recovered and purified prior to use. Recovery and purification techniques are well known and will not be dealt with here.

C. Compositions and Process

As noted elsewhere, immune system leukocyte effector or inflammatory cells such as monocytes, T cells and eosinophils bear the VLA-4 receptor on their cell surfaces. Those cells bind to the CS-1 portion of fibronectin present on the surfaces of vascular endothelial cells at an early step in inflammatory cell emigration (trafficking) from the blood in the tissues. These inflammatory cells immunoreact with monoclonal antibody P4C2 discussed in Wayner et al., *J. Cell. Biol.*, 109:1321–1330 (1989), Wayner WO 98/12809, Hemler et al, *J. Biol. Chem.*, 262(24):11478–11485 (1987) and monoclonal antibody HP1/2 of Lobb WO 93/13798 published Jul. 22, 1993.

Once in the tissues, the inflammatory cells enhance the inflammatory response through one or more of several mechanisms. In one mechanism, cytokines and chemoattractants reactants such as interleukin-1$\beta$ (IL-1$\beta$), IL-2, tumor necrosis factor $\alpha$ (TNF$\alpha$) and lymphocyte-derived chemotactic factor are released by the inflammatory cells and cause further inflammatory cells to emigrate to the area. In another mechanism, the inflammatory cells mis-recognize cells of the mammal with the inflammatory disease state as being non-self and attack those cells, killing them. These and other mechanisms of immunoinflammatory response enhancement are well known to skilled workers and need not be further elaborated upon here. The fibronectin CS-1 peptide thus mediates inflammatory disease states by assisting emigration of inflammation-enhancing effector cells from the blood into the tissues.

A contemplated inhibitor peptide blocks binding between CS-1 and VLA-4, and inhibits the resulting emigration of inflammatory cells bearing VLA-4 receptors into the tissues, and the exacerbation of the inflammatory condition that results. That inhibition of emigration of inflammatory cells results in a reduction of the fibronectin CS-1/VLA-4-mediated inflammatory response caused by those inflammatory cells, and thereby reduces the observed inflammation.

Particular inflammatory disease states that are mediated by CS-1 and VLA-4, and in which a contemplated inhibitor peptide can diminish inflammation are quite broad. Illustrative of those types of inflammation are asthma, arthritic conditions such as rheumatoid arthritis and osteoarthritis, allograft rejection, various types of skin inflammation, and demyelinating diseases of the central nervous system.

Specific pathological inflammatory conditions in which expression of CS-1 has been found to be implicated and where no such expression is observed in absence of a pathological condition (i.e., in normal tissue) include: rheumatoid arthritis (synovium), osteoarthritis (synovium), skin psoriasis, kidney transplant, asthmatic lung, and lymph node high endothelial venules (HEV) in humans, as well as in the gut of monkeys infected with SIV and those having inflammatory bowel disease, rabbits having asthmatic lungs and heart transplants, mouse brain in experimental autoimmune encephalomyelitis (EAE) and skin in delayed type hypersensitivity (DTH), and the joints of rats with induced arthritis.

A pharmaceutical composition containing a contemplated inhibitor peptide dissolved or dispersed in a pharmaceutically acceptable carrier or diluent that is preferably aqueous is also contemplated for use in treating a CS-1/VLA-4-mediated inflammatory disease state such as those discussed before. Such a composition contains a CS-1/VLA-4 binding-inhibiting (an inflammation-reducing) amount of a before-discussed, contemplated inhibitor peptide.

Thus, the present invention also contemplates a pharmaceutical composition that can be used in treating the aforementioned conditions. A contemplated pharmaceutical composition is comprised of a before-described inhibitor peptide that inhibits the binding interaction between VLA-4-containing leukocytes and the fibronectin peptide CS-1 portion expressed on endothelial cell surfaces, which peptide is dissolved or dispersed in a pharmaceutically acceptable diluent in a binding inhibitory (inflammation-reducing) amount. A contemplated pharmaceutical composition is suitable for use in a variety of drug delivery systems. For a brief review of present methods for drug delivery, see, Langer, *Science,* 249:1527–1533 (1990).

For a contemplated pharmaceutical composition, the dose of the peptide varies according to, e.g., the particular peptide, the manner of administration, the particular disease being treated and its severity, the overall health and condition of the patient, and the judgment of the prescribing physician or veterinarian. A pharmaceutical composition is intended for parenteral, topical, oral or local administration, such as by aerosol or transdermally, for prophylactic and/or therapeutic treatment. A pharmaceutical composition can be administered in a variety of unit dosage forms depending upon the method of administration. For example, unit dosage forms suitable for oral administration include powder, tablets, pills, capsules and dragees.

Preferably, a pharmaceutical composition is administered intravenously. Thus, a composition for intravenous administration is particularly contemplated that comprises a solution of a contemplated inhibitor peptide dissolved or dispersed in a pharmaceutically acceptable diluent (carrier), preferably an aqueous carrier. A variety of aqueous carriers can be used, e.g., water, buffered water, 0.9 percent saline, buffered aqueous ethanol solutions and the like. These compositions can be sterilized by conventional, well known sterilization techniques, or can be sterile filtered. The resulting aqueous solutions can be packaged for use as is, or lyophilized, the lyophilized preparation being combined with a sterile aqueous solution prior to administration. A composition can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of inhibitor peptide utilized is usually at or at least about 0.0001 percent to as much as about 0.1 percent by weight and is selected primarily by fluid volumes, viscosities, etc., in accordance with the particular mode of administration selected.

Thus, a typical pharmaceutical composition for intravenous infusion can be made up to contain 250 ml of sterile Ringer's solution normal saline or PBS, and up to about 2.5 mg of the inhibitor peptide. Actual methods for preparing parenterally administrable compounds are known or apparent to those skilled in the art and are described in more detail in for example, *Remington's Pharmaceutical Sciences,* 17th ed., Mack Publishing Company, Easton, Pa. (1985), which is incorporated herein by reference.

For solid compositions, conventional nontoxic solid diluents (carriers) may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95 percent of active ingredient, that is, a before-described inhibitor peptide preferably about 20 percent (see, *Remington's,* supra), preferably using an enteric coating to pass a solid dose through the stomach and into the intestine.

For aerosol administration, a contemplated inhibitor peptide is preferably supplied in solution such as aqueous ethanol or DMSO solution along with a surfactant and propellant. Typical percentages of an inhibitor peptide are about 0.0001 percent to about 0.1 percent by weight, and preferably about 0.0001 percent to about 0.001 percent. The surfactant must of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol, and the polyoxyethylene and polyoxypropylene derivatives of these esters. Mixed esters, such as mixed or natural glycerides can be employed. The surfactant can constitute about 0.1 to about 20 percent by weight of the composition, and preferably about 0.25 to about 5 percent. The balance of the composition is ordinarily propellant. Liquefied propellants are typically gases at ambient conditions, and are condensed under pressure. Among suitable liquefied propellants are the lower alkanes containing up to 5 carbons, such as butane and propane; and preferably fluorinated or fluorochlorinated alkanes. Mixtures of the above can also be employed. In producing the aerosol, a container equipped with a suitable valve is filled with the appropriate propellant, containing the finely divided compounds and surfactant. The ingredients are thus maintained at an elevated pressure until released by action of the valve.

A pump-activated spray using air as propellant (atomizer or nebulizer) is also contemplated.

For example, for the treatment of asthma in rabbits, the dose of a contemplated peptide is in the range of about 1 to 100 mg/day for a 2–3 kg animal. For a human asthma patient, that dose is in the range of about 1 to about 100 mg/day for a 70 kg patient. Administration for asthma is typically by aerosol from a nebulizer. Ideally, therapeutic administration should begin as soon as possible after the attack begins.

A pharmaceutical composition containing an inhibitor peptide can be administered for prophylactic and/or therapeutic treatments. In therapeutic applications, a composition is administered to a patient already suffering from a disease, as described above, in an amount sufficient to inhibit binding between VLA-4-expressing leukocytes and endothelial cells that express the CS-1 peptide portion; i.e., reduce inflammation and thereby at least partially arrest the symptoms of the disease and its complications. An amount adequate to accomplish this is defined as "therapeutically effective dose", or a "binding-inhibiting amount" or an "inflammation-reducing amount". Amounts effective for this use depend on the severity of the disease and the weight and general state of the patient, but generally range from about 1 mg/kg to about 500 mg/kg of inhibitor peptide per day, with dosages of from about 1 mg/kg to about 10 mg/kg of a compound per day being more commonly used.

In prophylactic applications, a composition containing a contemplated peptide is administered to a patient susceptible to or otherwise at risk of a particular disease. Such an amount is defined to be a "prophylactically effective dose" and is also an amount sufficient to inhibit binding of VLA-4-expressing leukocytes to CS-1 peptide-expressing endothelial cells. In this use, the precise amounts again depend on the patient's state of health and weight, but generally range from about 1 mg/kg/day to about 500 mg/kg/day, more commonly from about 1 mg/kg/day to about 20 mg/kg/day.

Another way to assess a binding-inhibiting amount of a contemplated inhibitor peptide is to compare binding inhibition exhibited by the peptide to that provided by CS-1 or the 10-mer standard in an in vitro study. One convenient way to make that comparison is by use of $IC_{50}$ values of the two compared materials, and base the amount used on the amount of CS-1 or standard 10-mer peptide and an amount of the inhibitor peptide that is a multiple of the $IC_{50}$ value for that reference compound.

Typically, a compound whose $IC_{50}$ value is at least about one-tenth that of the standard 10-mer (ten-times more potent), when used at one-tenth the molar amount of the 10-mer standard is a useful binding-inhibiting amount. More preferably, the amount is about one-fiftieth the amount of the 10-mer. More preferably still, the amount is equal to about one-hundredth that of the 10-mer. Inasmuch as those amounts inhibit binding by about 50 percent, greater concentrations that inhibit binding still further are preferred.

Thus, for in vitro use, a minimal CS-1/VLA-4-inhibiting amount is the $IC_{50}$ value. For in vivo use, the CS-1/VLA-4-inhibiting amount usually used begins with the $IC_{50}$ value concentration, and can decrease as required or one can increase to the solubility limit of the peptide in the utilized aqueous medium; i.e., the aqueous medium at pH 7.2–7.4 used such as normal saline where parenteral administration is used or intestinal fluid where oral administration is used.

Single or multiple administrations of a composition can be carried out with dose levels and pattern being selected by the treating physician or veterinarian. In any event, a pharmaceutical composition is formulated to provide a quantity of an inhibitor peptide sufficient to effectively treat the patient.

A process for treating fibronectin CS-1/VLA-4-mediated inflammation is also contemplated. In accordance with such a process, a before-described, contemplated inhibitor peptide is administered to a mammal in need of such a treatment such as a mammal having such inflammation or prophylactically as prior to an allograft. This administration is preferably via a before-discussed pharmaceutical composition. The peptide is administered in an inflammation-reducing (CS-1/VLA-4 binding inhibiting) amount. The mammal such as mouse, rat, rabbit, monkey or human is maintained until the peptide is eliminated by a natural bodily process. Multiple administrations in a single day, over a period of days or weeks, or for the life of the host mammal, where the mammal is the recipient of an allograft, are contemplated, as are single administrations.

Methods for determining an amount sufficient to inhibit binding between CS-1 and VLA-4 have already been discussed, particularly for in vitro studies. For in vivo uses, there are many published assays to determine if inflammation has been reduced by a particular treatment. For example, one can assess the number of painful joints in an arthritic patient or the patient's mobility before and after treatment. Reduction of effects of an asthma attack can be assayed by measurement of dynamic compliance or lung resistance in laboratory animals as is also well known. The amount of edema observed in DTH is also readily measurable, as are the effects of allograft rejection or its absence compared to standard controls.

BEST MODE FOR CARRYING OUT THE INVENTION

EXAMPLE 1

Synthesis of X-Leu-Asp-Phe-Z

Protected amino acids, Boc-Phe-OH, Boc-Asp(OBn)-OH and Boc-Leu-OH were purchased from NOVA Biochem Co., La Jolla, Calif. and were used without further purification. Phenylacetic acid, morpholine, diisopropylethylamine (DIEA) and 1-hydroxybenztriazole (HOBt) were obtained from Aldrich Chemical Co., Milwaukee, Wis. Ethyl-3-(3-dimethylamino)propylcarbodiimide.HCl (EDC) was obtained from Bachem Co., Torrance, Calif. 4 Normal HCl in dioxane was obtained from Pierce Co., Rockford, Ill. used as received.

The $^1$HNMR spectra were recorded on a GE QE-300, 300 MHz NMR spectrometer.

A. Preparation of Boc-Phe-Morpholinamide

A 250 ml flask was charged with Boc-Phe-OH (10 g, 38 mmol), morpholine (3.3 g, 38 mmol) and 1-hydroxybenztriazole (5.1 g, 38 mmol) in 100 ml dry dimethylformamide (DMF). To this solution was added diisopropylethylamine (DIEA) at zero degrees C. until the pH value reached 8, followed by addition of EDC (8.8 g, 46 mmol). The solution was slowly warmed to room temperature. The mixture was stirred for eight hours at room temperature (about 22° C.). The DMF was removed by vacuum evaporator, ethyl acetate and water were added, and the layers were separated. The aqueous layer was extracted with ethyl acetate (50 ml×2), combined extracts were washed with 1N HCl, saturated $NaHCO_3$, water and brine, dried with $MgSO_4$, filtered and concentrated to give a colorless liquid (12.8 g, 37.7 mmol; 99 percent yield) that was characterized by $^1$HNMR as Boc-Phe-morpholine.

B. Preparation of HCl-Phe-Morpholinamide Salt

Boc-Phe-morpholinamide (12.8 g, 38 mmol) was placed in a 250 ml flask, then 4N HCl in dioxane (30 ml) was added. The mixture was stirred for six hours at which time TLC (silica gel; $CHCl_3$:MeOH:acetic acid, 90:8:2) indicated that the reaction was completed. Dioxane and excess HCl were removed. A white solid, identified by $^1$HNMR as HCl-Phe-morpholinamide, was obtained in 100 percent yield (10.3 g, 38 mmol).

C. Preparation of N-Phenylacetyl-Leu-Asp(β-O-Benzyl)-Phe-Morpholinamide

Boc-Asp(β-OBn)-OH, Boc-Leu-OH and phenylacetic acid were sequentially added to HCl-Phe-morpholinamide using the coupling and deprotection procedures, described above. The white solid, thus obtained, was crystallized from ethyl acetate and hexane, and identified by $^1$HNMR as the desired ester in 95 percent yield.

D. Synthesis of N-Phenylacetyl-Leu-Asp(β-O-Bn)-Phe-Morpholinamide

To a solution of the above benzyl ester (10 g, 15 mmol) in methanol (100 ml) was added 10 percent palladium-charcoal (2.0 g). The flask containing this mixture was evacuated and then filled with hydrogen three times. The mixture was then vigorously stirred under a hydrogen atmosphere about five hours until the hydrogenalysis was complete, as indicated by TLC ($CHCL_3$:MeOH:acetic acid, 90:8:2). The reaction mixture was filtered through celite, and the methanol was removed, affording a white solid that was characterized by $^1$HNMR as XLDFZ (8.4 g, 14.5 mmol) in 97 percent yield.

Peptides having other than carboxamide [C(O)—$NH_2$] C-terminal amide-linked Z groups were similarly prepared.

EXAMPLE 2
Exemplary Solid Phase Peptide Syntheses

Fmoc protected amino acids, hydroxybenzotriazole (HOBt) and Rink amide MBHA resin were obtained from Nova Biochem, La Jolla, Calif. Diisopropylcarbodiimide (DIC) was obtained from Chem Impex Inc., Chicago, Ill. Piperidine was obtained from Aldrich Chemical Company, St. Louis, Mo. Dimethylformamide (DMF), isopropanol (IPA), dichloromethane (DCM), and dimethylacetamide (DMA) were obtained from Burdick and Jackson, Muskegon, Mich. All of the above reagents were used as supplied by the manufacturer, with no further purification.

The standard deprotection/coupling cycle iterated during this synthesis is described in terms of the first coupling of Fmoc-Pro to the Rink amide MBHA resin:

The Fmoc-MBHA resin (10.6 g., 5 mmoles) was treated with 20 percent piperidine in DMF (130 ml) for three minutes. The solution was removed by filtration and the resin was again treated with 20 percent piperidine in DMF (130 ml) for 17 minutes. The solution was removed by filtration and the resin was washed five times with DMF (130 ml each), two times with IPA (130 ml) and two times with DMF (130 ml). The HOBt ester of Fmoc-D-proline (formed by reacting a solution of 10 mmoles Fmoc-D-proline and 10 mmoles HOBt in 50 ml DMA with 12 mmoles DIC for 20 minutes at room temperature), in DMA (50 ml), was added to the resin and allowed to react for two hours. The resin was washed five times with DMF (130 ml) and two times with DCM (130 ml). The coupling of amino acid to the resin was checked by standard Kaiser's test.

The above cycle was iterated for each of the subsequent amino acids: Fmoc-Phe, Fmoc-Asp(β-OBn), Fmoc-Leu, and phenylacetic acid. The resin was dried in vaccuo for 24 hours and then allowed to react with 95 percent TFA/5 percent $H_2O$ (60 ml) for two hours at room temperature. The TFA solution of the peptide was separated from the resin by filtration and the TFA was vacuum evaporated. The solid residue was crystallized from anhydrous ethanol to yield 1.8 g of product, N-phenylacetyl-Leu-Asp-Phe-D-Pro-$NH_2$. The peptide was characterized by amino acid analysis on HP Amino Quant 1090 and NMR, and the purity of the peptide was checked by HPLC (WATER HPLC Systems).

EXAMPLE 3
In Vitro Binding Assays

Jurkat cells (ATCC TIB 152), a human T lymphoblastic line, labeled with $^{51}$chromium were used to assay in vitro binding inhibition provided by various peptides discussed herein. Costar™ 96 well flat-bottom microtiter plates (catalog No. 9050, Cambridge, Mass.) were found to provide the best results in these assays.

The plates were prepared as follows: The 25-mer CS-1 peptide (SEQ ID NO:1) dissolved at 0.5–1 μg/ml in a buffer of 0.1M $NaHCO_3$ at pH 9.5 that also contained 10 μg/ml of bovine serum albumin (BSA) or a conjugate of the CS-1 peptide linked to ovalbumin (CS-1-OVA) dissolved at 1–2.5 μg/ml in the same buffer was used as the substrate. Each well of the microtiter plates was coated with 50 μl of substrate or buffer alone for controls. The wells were permitted to dry out completely and were then rinsed twice with PBS at pH 7.4. Non-specific binding sites of each well were then blocked using 200 μl per well of RPMI/1 percent BSA for two hours at room temperature. Both solid phase-affixed substrates provided similar results.

Jurkat cells (3–5×$10^6$ cells) were placed into a 15 ml Falcon™ round-bottom tube with a cap. The tube was centrifuged, and the extra medium was then removed.

Two hundred microliters of a $^{51}$Cr labeling solution were added to the centrifuged cells and maintained in contact with the cells for 90–120 minutes in a warm room. This procedure typically provides about 50,000–100,000 cpm/well with about 80–100 percent cell viability. Longer contact times provide a greater amount of labeling but lower cell viability.

The labeled cells are washed with (i) complete medium, (ii) 1 mM EDTA/PBS and then (iii) RPM1/1 percent BSA free of serum components. The cells are centrifuged after each washing. The cells are finally resuspended in serum-free RPMI/1 percent BSA at a concentration of 1×$10^6$ viable cells/ml, which provides a concentration that is diluted by one-half in the assay.

Inhibitor peptides are prepared as stock solutions at 20 mg/ml in DMSO in 1.5 ml cryogenic screwcap vials, and were stored at −70° C. Using Flow™ round-bottom or V-bottom microtiter plates, the inhibitor peptides were prepared at twice the assay concentration in RPMI/1 percent BSA at 60 μl/well.

Four initial dilutions were typically used. For less potent peptides such as the standard 10-mer of SEQ ID NO:3, the initial dilutions were 500 μg/ml, 100 μg/ml, 20 μg/ml and 4 μg/ml. For more potent peptides such as N-phenylacetyl-Leu-Asp-Phe-D-Pro-$NH_2$, the typical initial concentrations were 10 μg/ml, 2 μg/ml, 0.4 μg/ml and 0.08 μg/ml.

The $^{51}$Cr-labeled cells (1×$10^6$ cells at 60 μl/well) were then admixed with the diluted peptide solutions. The admixtures were maintained at room temperature (about 22° C.) for 30 minutes.

One hundred microliters of each inhibitor peptide/cell admixture were transferred to the substrate-coated wells. This was done in triplicate for each dilution. The resulting plates were incubated for 30 minutes at 37° C. and then washed gently three times with RPMI/1 percent BSA at 200 μl/well. Binding was observed microscopically, particularly after the second wash.

The bound cells were then lysed by the addition of a 0.5 percent solution of sodium dodecylsulfate in water at 100 μl/well. The resulting solutions were then processed for counting and calculation of $IC_{50}$ values following usual procedures. Appropriate positive and negative controls were used with each plate so that the results of separate assays could be normalized and compared.

The data of Table 1 are so normalized. The absolute $IC_{50}$ value for the peptide N-phenylacetyl-Leu-Asp-Phe-morpholinamide is 0.18–0.30 µM.

EXAMPLE 4
Delayed Type Hypersensitivity in Mice

An adoptive transfer delayed-type hypersensitivity murine model has been developed using splenic T cells primed to oxazolone. This model is discribed in Elices et al., *Clin. Exp. Rheum.,* 11(Suppl. 8):577–580 (1993), whose procedures were followed here.

Thus, BALB/c mice were shaved on the belly and painted (50 µl on the belly and 5 µl on each paw) with three percent oxazolone in acetone/olive oil (4:1) at days zero and 1. At day 5, the mice were sacrificed, their spleens removed, and splenic T cells were obtained via nylon wool columns.

Normal saline or saline containing $25 \times 10^6$/animal of the oxazolone-immune T cells were separately injected into naive mice. The mice were then challenged by painting 10 µl of 2 percent oxazolone onto one ear each. All procedures were carried out under sterile conditions and in endotoxing-free buffers.

Prior to challenge or saline injection, the mice were implanted with pumps that subcutaneously administered normal saline, normal saline containing the peptide N-phenylacetyl-Leu-Asp-Phe-D-Pro-$NH_2$ or normal saline containing a peptide with a scrambled sequence continually at 6 mg/kg/day for a 24-hour time period. The swelling diameter at the site of challenge or saline injection was measured with a microcaliper 24 hours thereafter.

Figure 5:
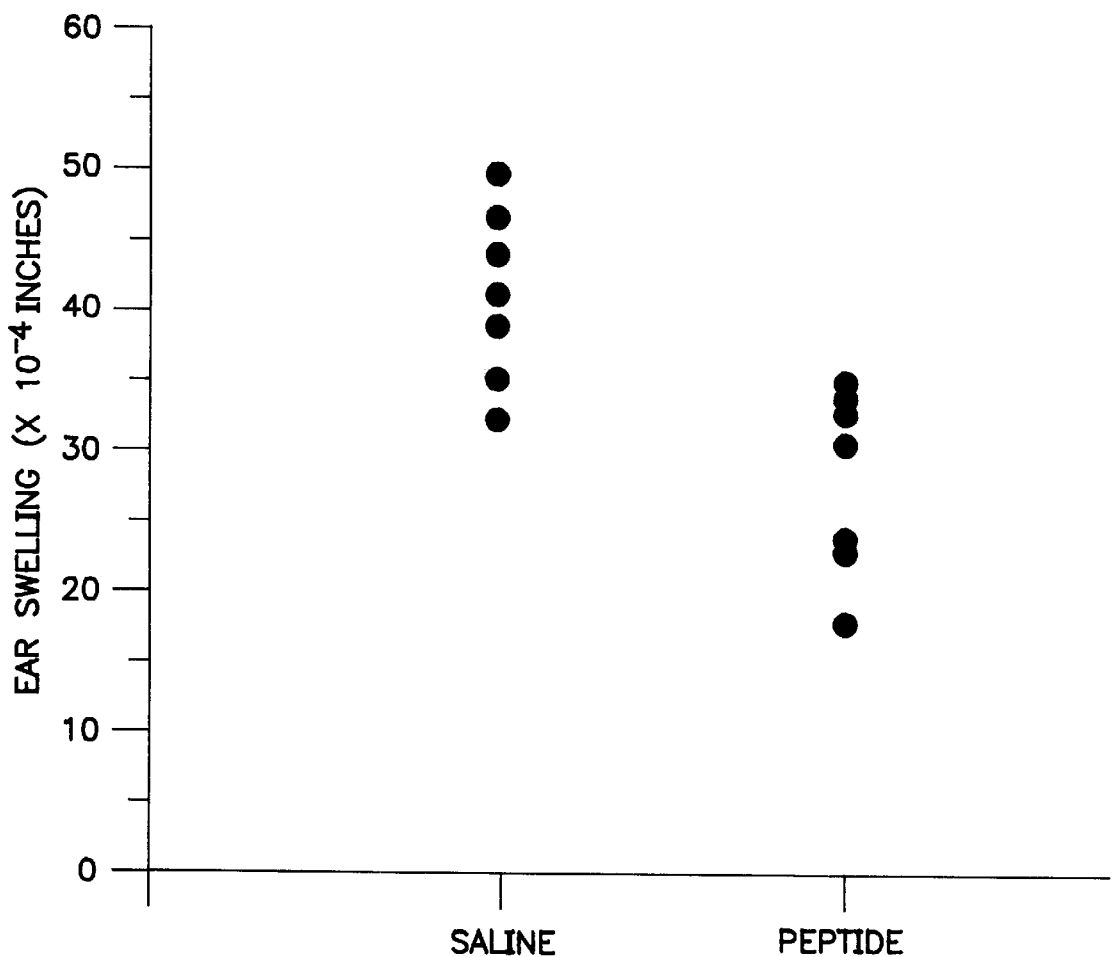
FIG. 5 is a graph showing the results of a study of the effect of the inhibitor peptide N-phenylacetyl-Leu-Asp-Phe-D-Pro-NH$_2$ on delayed type hypersensitivity measured in ears of 14 mice. After immunization, one group of seven mice was treated with only a saline solution provided by an implanted pump over a 24-hour time period and challenged. The other immunized group of seven mice was similarly challenged, but each was treated with an aqueous pharmaceutical composition containing the above inhibitor peptide for the same 24-hour time period, also supplied by implanted pumps. The ordinate is in units of inches of swelling diameter at the challenge site.

The results of this study are shown in the graph of FIG. 5 for the saline and recited inhibitor peptide treatments. Although there is a slight overlap in the data possibly due to non-CS-1-mediated inflammation, it is clear that administration of a contemplated inhibitor peptide reduced this type of CS-1/VLA-4-mediated immunoinflammation as compared to the untreated controls. Use of the scrambled peptide provided no reduction of inflammation. Another study using 600 mg/kg/day of the same peptide showed no toxicity caused by the peptide.

EXAMPLE 5
Treatment of Asthmatic Rabbits

Six New Zealand white rabbits were immunized with house dust mite antigen from birth through four months of age. Upon immunization, three rabbits received a single nebulizer administration of the inhibitor peptide N-phenylacetyl-Leu-Asp-Phe-morpholinamide in aqueous 50 percent ethanol as diluent in an amount of 100 mg/kg, and the other three received diluent alone. All of the rabbits were challenged with house dust mite antigen about 15–30 minutes after administration of the peptide, with those animals not receiving peptide serving as controls.

Once immunized and challenged, the inflammatory state subsides to a basal level within about three weeks. The three animals used as controls were thereafter used as subjects for receipt of an inhibitor peptide, and the three rabbits that initially received the peptide can serve as controls.

Such a crossover study was done here. Thus, the three initial control rabbits were treated with the above inhibitor peptide in the above diluent at a time more than three weeks after the above study, and the three previous recipients of the peptide were administered the diluent alone. All six were than challenged again.

Initial pulmonary function, measured by dynamic compliance ($C_{dyn}$) and lung resistance ($R_L$), and bronchoalveolar lavage (BAL) to obtain an effector cell count, here eosinophils, were conducted prior to administration of the peptide or diluent for both portions of this crossover study. Similar assays were then taken one-half hourly after challenge for six hours (early phase allergic reaction) and at 24 hours after challenge (late stage allergic reaction) for both portions of this study.

These studies were conducted by Dr. W. J. Metzger of East Carolina University, Greenville, N.C. as described by W. J. Metzger in *CRC Handbook of Late Phase Reactions,* W. Dorsch, ed., Chapter 35, CRC Press, Boca Raton, Fla. (1990) pages 347–362.

Figure 4A:
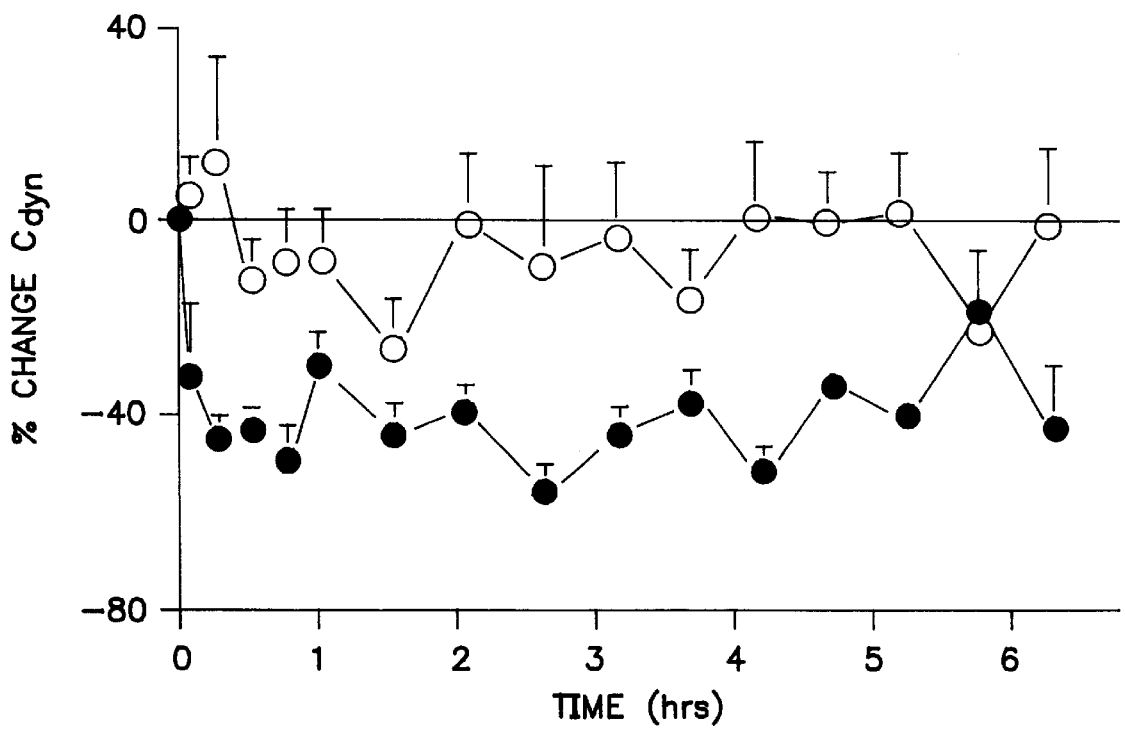
FIG. 4A shows the percent change in dynamic compliance ($C_{dyn}$) over a six-hour time period immediately following the onset of induced asthma attacks. Data for rabbits treated by a nebulized composition containing the inhibitor peptide N-phenylacetyl-Leu-Asp-Phe-morpholinamide are shown as open circles, whereas data for untreated rabbits are shown with darkened circles; both circles including error bars. The ordinate is in units of percent change from the initial dynamic compliance value, whereas the abscissa is in units of hours after challenge.
Figure 4B:
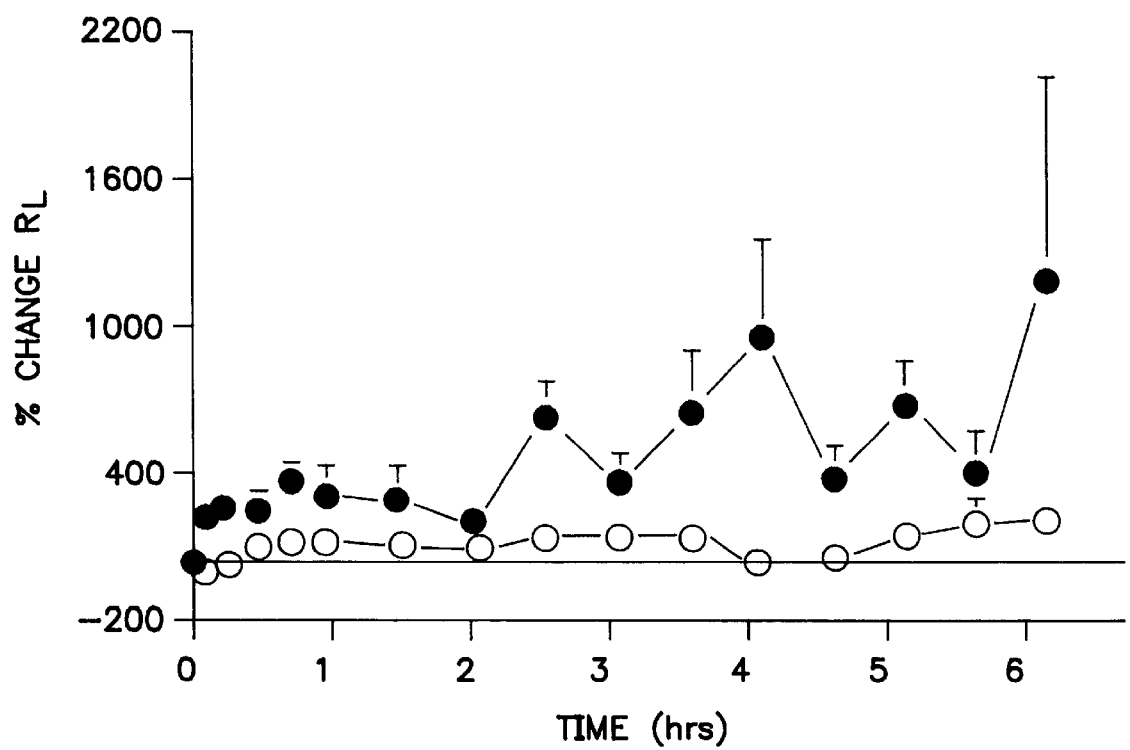
FIG. 4B illustrates the effects of a contemplated peptide in treating asthma in the rabbit.

The results of this study for the pulmonary function parameters are shown in FIG. 4A and FIG. 4B, in which data for the challenged, inhibitor peptide-treated animals are shown as open circles and data for the challenged, untreated, control animals are shown in blackened circles. These data are averaged values from both portions of the study.

As is seen from FIG. 4A, the $C_{dyn}$ value for the challenged and treated animals stayed at about the initial value for the whole six hours. The $C_{dyn}$ for the challenged, untreated animals quickly fell to about 40 percent of the initial value and then stayed at about that value for the whole six hours.

The data of FIG. 4B show that the $R_L$ values for the challenged, inhibitor peptide-treated animals remained between the initial value and about 200 percent of that value for the whole six hours, with a slight rise near the end of that time period. The $R_L$ values for the challenged, but untreated animals rose to about 200–300 percent in the first two hours after challenge and rose to about 400–1200 percent for the last four hours.

A summation of the averaged data for the inhibitor-treated, challenged animals compared to the challenged control animals for early (2–4 hours) and late (24 hours) phases of this inflammatory immune response is provided in Table 2, below.

TABLE 2

| IN VIVO Efficacy of φAc-Leu-Asp-Phe-Morph* | | |
|---|---|---|
| Parameter | Phase | % Reduction |
| $C_{dyn}$ | Early | 94.4 |
|  | Late | 86.6 |
| $R_L$ | Early | 80.1 |
|  | Late | 82.6 |

*N-Phenylacetyl-Leu-Asp-Phe-morpholinamide

The BAL count from these studies indicated an 88.1 percent reduction in eosinophils after 24 hours in the inhibitor peptide-treated, challenged animals as compared to the untreated, challenged animals in the crossover study.

As can be seen from the above data and those of FIGS. 4A and 4B, aerosol administration of an inflammation-reducing amount of a contemplated peptide greatly reduced the asthmatic response in the treated animals as compared to those receiving no treatments.

EXAMPLE 6
Rabbit Cardiac Allograft Model

New Zealand white rabbit SPF hearts were allografted into the necks of similar rabbits to assay a graft-vs-host immunorejection model and the affect of a contemplated peptide on that immunoinflammatory response. These studies were carried out by Dr. M. Rabinovitch of the Hospital for Sick Children, Toronto, Ontario, Canada.

Here, two rabbits were injected on day zero with 1 mg/kg/day of the inhibitor peptide N-phenylacetyl-Leu- Asp-Phe-D-Pro-NH$_2$ in aqueous diluent. The two rabbits then each received a grafted heart, with the graft being made in the carotid artery to the aorta of the grafted heart, and the jugular vein to the pulmonary artery of the grafted heart. The rabbits thereafter received daily injections of the same dose of that peptide, and were sacrificed on day 7. Another animal that received normal saline injections in place of the peptide injections, also received a similarly allografted heart, and was similarly sacrificed at day 7.

The animals' blood vessels were thereafter examined histologically for evidence of arteriopathy, and particularly thickening of the intimal elastic lamina (IEL) layer of the coronary arteries. Thickening of the IEL is caused at least in part by emigration of effector cells bearing the CD2 marker such as T cells and NK cells. Clausell et al., *Am. J. Path.*, 142(6):1772–1786 (1993).

These rabbits were maintained on a high fat diet to help accelerate the effects of rejection. As a result of the diet, basal levels of IEL thickening and lesion severity were elevated relative to rabbits fed on a normal diet. Basal levels were assayed in the coronary arteries of the hearts of recipient animals, whereas IEL thickening and lesion severity are assayed in the coronary arteries of the grafted hearts.

Upon examination of 114 vessels of the saline-treated rabbit, about 80 percent of the vessels exhibited IEL thickening. Similar evaluation of 141 vessels from the two rabbits that received the inhibitor peptide treatment showed that only about 30 percent of the vessels exhibited IEL thickening. These percentages can be compared to a basal IEL thickening of about 20 percent of the vessels.

An examination of the percentage of IEL thickening based on the total coronary vessel area, as a measure of the severity of the lesions, was also undertaken. Here, examination of 58 vessels of the saline-treated animal provided a value of 35 percent, whereas examination of 59 vessels from the two inhibitor peptide-treated rabbits showed a value of about 18 percent. The basal value here was about 15 percent.

Again, the CS-1/VLA-4-mediated immunoinflammatory response, here caused by allografts, was greatly reduced by administration of a contemplated inhibitor peptide to the host mammal, a rabbit.

EXAMPLE 7
In Vitro Porcine Allograft Model

A similar study was carried out in vitro using porcine coronary artery endothelial cells (EC; as are present in the IEL) and smooth muscle cells (SMC; as are present in the medial layer of the artery). The two cell types were cultured using a membrane transwell system, with the SMC on the bottom layer in M-199 medium (Gibco Labs.). The SMC were stimulated with 100 ng/ml of interleukin-1β (IL-1β) for 24 hours prior to the start of the assay. Porcine peripheral blood lymphocytes were separated by Ficoll-Hypaque, radiolabeled and incubated overnight (about 18 hours) on the EC.

Transendothelial lymphocyte migration in the IL-1β-stimulated SMC was observed as compared to unstimulated SMC (p<0.05). The inhibitor peptide of Example 6, phenylacetyl-Leu-Asp-Phe-D-Pro-NH$_2$, present at 10 μg/ml in the medium reduced lymphocyte migration by about 30 percent (p<0.05), whereas the same amount of a control peptide whose sequence was scrambled did not reduce migration.

Increased expression of EC and SMC fibronectin and IL-1β are features of an immunoinflammatory response associated with accelerated graft arteriopathy following piglet heterotopic cardiac transplantation. The above results indicate that IL-1β induces fibronectin production in this in vitro model, which in turn contributes to transendothelial lymphocyte migration. The above results also illustrate that a contemplated inhibitor peptide can be used to reduce this immunoinflammatory response.

EXAMPLE 8
Experimental Autoimmune Encephalomyetlitis in Mice

Experimental autoimmune encephalomyelitis (EAE) is a demyelinating disease of the central nervous system that can be induced in susceptible strains of mice and rats by immunization with myelin basic protein, proteolipid protein (PLP), or their immunodominant T cell determinants, or by injection of CD4-positive T cell clones specific for those determinants. EAE serves as an animal model of human multiple sclerosis. In both diseases, circulating leukocytes such as T cells and monocytes penetrate the blood/brain barrier and damage myelin, resulting in paralysis.

EAE was induced in female SJL/J mice (8 to 14 weeks old) by immunization on day zero with 50 μg of a peptide corresponding to positions 139–151 of PLP emulsified in a 1:1 mixture of PBS and complete Freund's adjuvant (CFA). Each mouse was injected with 0.2 ml of the adjuvant emulsion subcutaneously (s.c.) at two sites in the hind flank. All mice received $10^7$ killed *Bordetella pertussis* units in 100 μl were injected intravenously 24 to 72 hours later.

Mice were observed daily, beginning at day 8 for clinical signs of EAE, and disease was scored on a scale of 0–5 as: 0=no disease; 1=floppy tail; 2=moderate hind limb weakness; 3=paraparesis; 4=paraplegis with moderate forelimb weakness; 5=qualdriplegis or premoribund state.

The inhibitor peptide N-phenylacetyl-Leu-Asp-Phe-D-Pro-NH$_2$ was administered intraperitoneally at 1 mg/mouse in 0.2 ml of incomplete Freund's adjuvant at days 8 and 9. A peptide having a scrambled sequence [N-phenylacetyl-Asp-Leu-Phe-D-Pro-NH$_2$] was similarly administered to serve as a control. The relative potency of this control peptide is shown in Table 1 to be <1.

Summed or averaged scores for clinical signs were plotted vs. time. The area under the resulting curves was calculated between day 8 and day 35 to calculate percentage inhibition of EAE by an inhibitor peptide. The percent inhibition was calculated as follows:

% Inhibition=100–(Area of inhibitor peptide÷control area)×100

Figure 6:
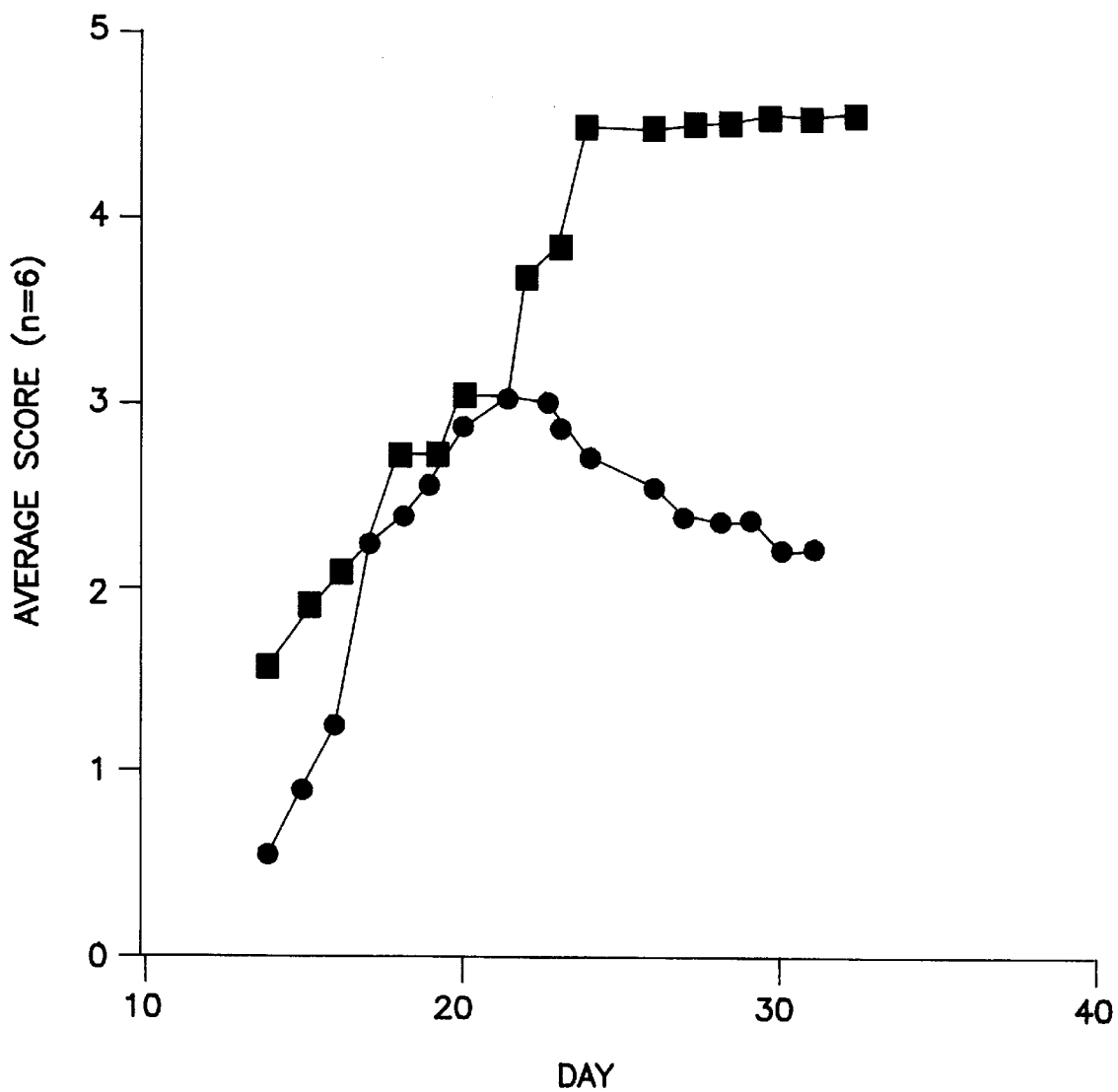
FIG. 6 is a graph showing averaged clinical scores for six mice each in two evaluations of treatments of experimental autoimmune encephalomyelitis (EAE). Darkened circles are for treatments using the inhibitor peptide N-phenylacetyl-Leu-Asp-Phe-D-Pro-NH$_2$, whereas points shown as darkened squares are for treatments using the scrambled sequence peptide N-phenylacetyl-Asp-Leu-Phe-D-Pro-NH$_2$. The ordinant shows the averaged score for the six mice in each study, whereas the abscissa is in days after initiation of EAE.

Two exemplary plots through day 31 are shown in the graph of FIG. 6 in which the darkened circles are averaged scores for six mice treated with the inhibitor peptide and darkened squares are averaged scores for six mice that received the scrambled sequence control peptide. As can be seen, animals treated with an inhibitor peptide contemplated herein exhibited marked improvement in clinical signs as compared to those animals treated with the control peptide.

EXAMPLE 9
CS-1 Expression in Human Rheumatoid Arthritis

Surgically-obtained synovial specimens from human rheumatoid arthritis (RA) patients were examined microscopically for the expression of the CS-1 peptide portion of fibronectin. Ultrathin sections of tissue were stained by the immunoperoxidase technique using anti-CS-1 antibodies, and were studied using transmission electron microscopy. These studies showed that CS-1 was expressed on the lumenal aspect of blood vessel endothelium, on the lumenal plasma membrane. The plasma membrane of synoviocytes in the synovial intimal lining at the interface with the joint space was also stained. The CS-1 peptide portion was not found to be expressed in normal synovium.

Binding studies were carried out using the Jurkat T cell line and frozen RA synovial sections. Jurkat cell adhesion could be inhibited by anti-VLA-4 antibodies or the 10-mer CS-1 peptide portion (500 μg/ml) used as standard here (SEQ ID NO:3), but not with antibodies to VLA-5, VCAM-1-A or VCAM-1-B or a peptide in which the 10-mer sequence was scrambled. Stimulated MOLT-4 cells behaved similarly. These results are reported in Elices et al., *J. Clin. Invest.*, 93:405–416 (January 1994).

A similar inhibition of binding of Jurkat cells to human RA synovial sections and not to normal synovial sections was observed using the inhibitor peptide N-phenylacetyl-Leu-Asp-Phe-D-Pro-NH$_2$. That peptide was used at its IC$_{50}$ value shown in Table 1 to be about 312 times less than the IC$_{50}$ value for the standard 10-mer. The absolute value of that IC$_{50}$ value is about 0.5 μmolar.

These results illustrate the importance of the CS-1 peptide portion and VLA-4 in a human chronic immunoinflammatory disease state, rheumatoid arthritis. These results also show that a contemplated inhibitor cell can inhibit the binding of inflammatory cells in this human immunoinflammatory disease state.

Although the present invention has now been described in terms of certain preferred embodiments, and exemplifed with respect thereto, one skilled in the art will readily appreciate that various modifications, changes, omissions and substitutions may be made without departing from the spirit thereof.

We claim:

1. A peptide of formula I $$X\text{-Leu-Asp-}Z \qquad I$$

wherein

X is a group amide-linked to the nitrogen atom of Leu, said group having a ring structure bonded to the carbonyl carbon of said amide-linkage by a spacer having a length of zero to about two methylene groups, said ring structure being a 5-membered ring, a 6-membered ring, a 6-membered ring fused to another 6-membered ring, or a 6-membered ring fused to a 5-membered ring, the length of X, including said spacer and carbonyl carbon, being about that of 3-quinolinecarbonyl or smaller, unless; (i) said ring structure of X is substituted with a $C_1$–$C_2$ alkyl or hydroxyl group, (ii) the α-amino group of the X amino acid residue is acylated with a $C_1$–$C_6$ acyl group or (iii) X together with the nitrogen atom of said Leu forms a phthalimido, a 1,2,3,4-tetrahydroquinazoline-2,4-dione-3-yl or 5-phenylhydantoin-3-yl group; and Z is Xaa-$NCy^1$ where Xaa is Val, Ile, Leu or an amino acid residue having a side chain that contains one or two fused aromatic rings and $NCy^1$ is a cyclic ring-containing group having a ring nitrogen atom that forms an amide bond with the α-carboxyl group of Xaa, and whose cyclic ring contains 5- or 6-atoms including said ring nitrogen atom.

2. The peptide according to claim 1 wherein the ring structure of said X group contains an aromatic ring.

3. The peptide according to claim 2 wherein said aromatic ring is substituted with a $C_1$–$C_2$ alkyl or hydroxyl group.

4. The peptide according to claim 1 wherein Xaa is an amino acid residue having a side chain that contains one or two fused aromatic rings.

5. The peptide according to claim 4 wherein the cyclic ring of $NCy^1$ is substituted with one or two substituent groups selected from the group consisting of carboxyl, carboxamide, hydroxyl, hydroxymethyl and $C_1$–$C_4$ alkyl.

6. The peptide according to claim 1 wherein X is an amino acid residue having a cyclic ring side chain.

7. The peptide according to claim 6 wherein said amino acid residue is tryptophyl.

8. The peptide according to claim 6 wherein the nitrogen atom of the α-amino group of the X amino acid residue is acylated with a $C_1$-$C_6$ acyl group.

9. The peptide of claim 1 having the formula

Ar—Y—C(O)-Leu-Asp-Xaa-NCy$^1$ wherein

Ar is pyrazolyl, phenyl, dihydroxyphenyl, pyridyl, or 3-quinolinyl;

Y is said spacer that is absent, —CH$_2$—, —CH(NH)—, —O— or —NH—;

or Ar—Y—C(O)— together with the nitrogen atom of said Leu forms a phthalimido, a 1,2,3,4-tetrahydroquinazoline-2,4-dione-3-yl or 5-phenylhydantoin-3-yl group;

Xaa is an aromatic acid residue; and

NCy$^1$ is an amine-containing 5- or 6-membered cyclic ring group whose depicted nitrogen atom is within the ring and forms an amide bond with α-carboxyl of Xaa.

10. The peptide according to claim 9 wherein Y is absent.

11. The peptide according to claim 9 wherein Xaa is selected from the group consisting of phenylalanyl, tryptophyl and tyrosyl.

12. The peptide according to claim 9 wherein Ar—Y—C(O)— is a substituent selected from the group consisting of benzoyl, phenylacetyl, 3-pyridinecarbonyl, 4-pyridinecarbonyl, 3-pyridineacetyl, phenoxycarbonyl, anilinocarbonyl, pyrazolecarbonyl, and 3,4-dihydroxybenzoyl groups.

13. The peptide according to claim 9 wherein NCy$^1$ is selected from the group consisting of morpholinamino, 4-hydroxypiperidamino, L-2-(carboxamide)pyrrolidinamino, D-2-(carboxamide)pyrrolidinamino, pyrrolidinamino, 3,4-dihydroxypyrrolidinamino, 2-(hydroxymethyl)pyrrolidinamino and piperazinamino groups, and wherein the nitrogen atom within the ring of NCy$^1$ forms an amide bond with the α-carboxyl group of said Xaa.

14. The peptide according to claim 13 wherein Ar—Y—C(O)— together with the nitrogen atom of said Leu form a phthalimido group.

15. The peptide according to claim 9 having the formula phenylacetyl-Leu-Asp-Phe-NCy$^3$ wherein NCy$^3$ is selected from the group consisting of morpholinamino, D-2-(carboxamide)pyrrolidinamino, piperidinamino, piperazinamino, pyrrolidinamino and 4-hydroxypiperidinamino groups, and wherein the nitrogen atom within the ring of NCy$^3$ forms an amide bond with the α-carboxyl group of said Phe.

16. A pharmaceutical composition comprising a pharmaceutically acceptable carrier and the peptide of claim 15.

17. A pharmaceutical composition comprising a pharmaceutically acceptable carrier and the peptide of claim 2.

18. A pharmaceutical composition comprising a pharmaceutically acceptable carrier and the peptide of claim 4.

19. A pharmaceutical composition comprising a pharmaceutically acceptable carrier and the peptide of claim 9.

20. A pharmaceutical composition comprising a pharmaceutically acceptable carrier and the peptide of claim 1.

21. A process for treating inflammation that comprises administering to a mammal having said inflammation an inflammation-reducing amount of a peptide of claim 1.

22. The process according to claim 21 wherein said inflammation is asthma.

23. The process according to claim 21 wherein said administration is by inhalation.

24. The process according to claim 21 wherein said administration is parenteral.

25. The process according to claim 21 wherein said inflammation is rheumatoid arthritis or osteoarthritis.

26. The process according to claim 21 wherein said inflammation is allograft rejection.

27. The process according to claim 21 wherein said inflammation is a skin inflammation.

28. The process according to claim 21 wherein said inflammation is a central nervous system demyelinating disease.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 25 amino acids
      (B) TYPE: amino acid
      (D) TOPOLOGY: linear (ii) MOLECULE TYPE: peptide (xi) SEQUENCE DESCRIPTION: SEQ ID NO:1:

Asp Glu Leu Pro Gln Leu Val Thr Leu Pro His Pro Asn Leu His Gly
   1              5                     10                15

Pro Glu Ile Leu Asp Val Pro Ser Thr
              20                  25

(2) INFORMATION FOR SEQ ID NO:2:

(i) SEQUENCE CHARACTERISTICS:
      (A) LENGTH: 12 amino acids
      (B) TYPE: amino acid
      (D) TOPOLOGY: linear (ii) MOLECULE TYPE: peptide (xi) SEQUENCE DESCRIPTION: SEQ ID NO:2:

Leu His Gly Pro Glu Ile Leu Asp Val Pro Ser Thr
   1              5                     10

(2) INFORMATION FOR SEQ ID NO:3:

(i) SEQUENCE CHARACTERISTICS:
      (A) LENGTH: 10 amino acids
      (B) TYPE: amino acid
      (D) TOPOLOGY: linear (ii) MOLECULE TYPE: peptide (xi) SEQUENCE DESCRIPTION: SEQ ID NO:3:

Gly Pro Glu Ile Leu Asp Val Pro Ser Thr
   1              5                     10

(2) INFORMATION FOR SEQ ID NO:4:

(i) SEQUENCE CHARACTERISTICS:
      (A) LENGTH: 4 amino acids

```
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa= phenylacetyl-Leu."

(ix) FEATURE:
        (A) NAME/KEY: Modified-site
        (B) LOCATION: 4
        (D) OTHER INFORMATION: /label= Xaa
            /note= "Xaa= Pro-NH2."

(xi) SEQUENCE DESCRIPTION: SEQ ID NO:4:

Xaa Asp Tyr Xaa
    1

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = phenylacetyl-Leu."

(ix) FEATURE:
        (A) NAME/KEY: Modified-site
        (B) LOCATION: 4
        (D) OTHER INFORMATION: /label= Xaa
            /note= "Xaa = an amide formed between the
            C-terminal Pro carboxyl and a
            tetraethylenepentaamine containing 4

(xi) SEQUENCE DESCRIPTION: SEQ ID NO:5:

Xaa Asp Phe Xaa
    1

(2) INFORMATION FOR SEQ ID NO:6:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = GlcNAc-O-(CH2)5-C(O)-Phe."

(ix) FEATURE:
        (A) NAME/KEY: Modified-site
        (B) LOCATION: 4
        (D) OTHER INFORMATION: /label= Xaa
            /note= "Xaa = Leu-piperidinamide."

(xi) SEQUENCE DESCRIPTION: SEQ ID NO:6:

Xaa Leu Asp Xaa
    1
```

```
(2) INFORMATION FOR SEQ ID NO:7:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = benzoyl-Leu."

(ix) FEATURE:
        (A) NAME/KEY: Modified-site
        (B) LOCATION: 4
        (D) OTHER INFORMATION: /label= Xaa
            /note= "Xaa = Pro-NH2."

(xi) SEQUENCE DESCRIPTION: SEQ ID NO:7:

Xaa Asp Val Xaa
    1

(2) INFORMATION FOR SEQ ID NO:8:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = pivaloyl-Leu."

(ix) FEATURE:
        (A) NAME/KEY: Modified-site
        (B) LOCATION: 4
        (D) OTHER INFORMATION: /label= Xaa
            /note= "Xaa = Pro-NH2."

(xi) SEQUENCE DESCRIPTION: SEQ ID NO:8:

Xaa Asp Val Xaa
    1

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = phenylacetyl-Leu."

(ix) FEATURE:
        (A) NAME/KEY: Modified-site
        (B) LOCATION: 4
        (D) OTHER INFORMATION: /label= Xaa
            /note= "Xaa = Pro-decylamide."

(xi) SEQUENCE DESCRIPTION: SEQ ID NO:9:

Xaa Asp Phe Xaa
    1
```

(2) INFORMATION FOR SEQ ID NO:10:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /label= Xaa
            /note= "Xaa = Pro-NH2."

(xi) SEQUENCE DESCRIPTION: SEQ ID NO:10:

Ile Leu Asp Val Pro Ile Leu Asp Val Xaa
   1             5               10

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /label= Xaa
            /note= "Xaa = Pro-NH2."

(xi) SEQUENCE DESCRIPTION: SEQ ID NO:11:

Ile Leu Asp Phe Xaa
   1             5

(2) INFORMATION FOR SEQ ID NO:12:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /label= Xaa
            /note= "Xaa = phenylacetyl-Leu."

(ix) FEATURE:
        (A) NAME/KEY: Modified-site
        (B) LOCATION: 4
        (D) OTHER INFORMATION: /label= Xaa
            /note= "Xaa = Pro-NH(CH2)5-C(O)NHC18H37."

(xi) SEQUENCE DESCRIPTION: SEQ ID NO:12:

Xaa Asp Phe Xaa
   1

(2) INFORMATION FOR SEQ ID NO:13:

(i) SEQUENCE CHARACTERISTICS:
        (A) LENGTH: 5 amino acids
        (B) TYPE: amino acid
        (D) TOPOLOGY: linear (ii) MOLECULE TYPE: peptide

```
      (ix) FEATURE:
            (A) NAME/KEY: Modified-site
            (B) LOCATION: 5
            (D) OTHER INFORMATION: /label= Xaa
                 /note= "Xaa = Pro-NH2."

(xi) SEQUENCE DESCRIPTION: SEQ ID NO:13:

Ile Leu Asp Val Xaa
      1               5

(2) INFORMATION FOR SEQ ID NO:14:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:14:

Ile Leu Asp Val Pro
      1               5

(2) INFORMATION FOR SEQ ID NO:15:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /label= Xaa
                 /note= "Xaa = acetyl-Ser."

(ix) FEATURE:
            (A) NAME/KEY: Modified-site
            (B) LOCATION: 5
            (D) OTHER INFORMATION: /label= Xaa
                 /note= "Xaa = Ser-NH2."

(xi) SEQUENCE DESCRIPTION: SEQ ID NO:15:

Xaa Phe Asp Phe Xaa
      1               5
```